US008887368B2

(12) United States Patent
Mastalish et al.

(10) Patent No.: US 8,887,368 B2
(45) Date of Patent: *Nov. 18, 2014

(54) METHOD FOR ASSEMBLING A TAMPON APPLICATOR

(71) Applicant: Kimberly-Clark Worldwide, Inc., Neenah, WI (US)

(72) Inventors: Gary Michael Mastalish, Oshkosh, WI (US); Marcus David Weiher, Sherwood, WI (US); Gary Alan Turchan, Greenville, WI (US); Thomas William VanDenBogart, Slinger, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/888,958

(22) Filed: May 7, 2013

(65) Prior Publication Data

US 2013/0239394 A1    Sep. 19, 2013

Related U.S. Application Data

(63) Continuation of application No. 13/024,355, filed on Feb. 10, 2011, now Pat. No. 8,458,882.

(51) Int. Cl.
| A61F 13/26 | (2006.01) |
| A61F 13/20 | (2006.01) |
| B21D 39/04 | (2006.01) |
| A61F 13/551 | (2006.01) |

(52) U.S. Cl.
CPC ....... *A61F 13/55185* (2013.01); *A61F 13/2097* (2013.01); *A61F 13/26* (2013.01); *Y10S 604/904* (2013.01)
USPC .................. 29/434; 29/505; 604/11; 604/15; 604/904

(58) Field of Classification Search
USPC ........ 29/434, 505; 604/11, 13, 14, 15, 16, 18, 604/904
See application file for complete search history.

(56) References Cited

U.S. PATENT DOCUMENTS

| 4,536,178 | A | 8/1985 | Lichstein et al. |
| 4,973,302 | A | 11/1990 | Armour et al. |
| 5,158,535 | A | 10/1992 | Paul et al. |
| 7,066,870 | B2 | 6/2006 | Fedyk et al. |
| 8,458,882 | B2 * | 6/2013 | Mastalish et al. ............... 29/434 |
| 2004/0054317 | A1 | 3/2004 | Lemay et al. |
| 2004/0199102 | A1 | 10/2004 | Lemay et al. |
| 2010/0016780 | A1 | 1/2010 | Vandenbogart et al. |
| 2010/0324468 | A1 | 12/2010 | Gann et al. |

FOREIGN PATENT DOCUMENTS

| GB | 2 033 754 A | 5/1980 |
| WO | WO 88/08693 A1 | 11/1988 |
| WO | WO 04/000186 A2 | 12/2003 |

* cited by examiner

*Primary Examiner* — Jermie Cozart
(74) *Attorney, Agent, or Firm* — Kimberly-Clark Worldwide, Inc.

(57) ABSTRACT

A method of assembling a tampon applicator includes providing a barrel with internal ridges that define a guide channel having an effective diameter. The method includes providing a plunger that has a finger flare with a circular shape and a flare diameter that is at least 15% larger than the effective diameter of the guide channel. The method includes assembling the plunger and the barrel by pushing the finger flare into the guide channel and deforming the finger flare into a non-circular shape while moving the finger flare through the guide channel. The method includes moving the finger flare out of the plunger end of the barrel and reestablishing the circular shape of the finger flare.

21 Claims, 23 Drawing Sheets

METHOD FOR ASSEMBLING A TAMPON APPLICATOR

This application is a continuation of prior application Ser. No. 13/024,355, filed in the U.S. Patent and Trademark Office on Feb. 10, 2011 now U.S. Pat. No. 8,458,882 B2. The entirety of application Ser. No. 13/024,355 is hereby incorporated by reference in this application.

BACKGROUND OF THE INVENTION

The present invention relates generally to tampon applicators.

Vaginal tampons are disposable absorbent articles sized and shaped for insertion into a woman's vaginal canal for absorption of body fluids generally discharged during the woman's menstrual period. Insertion of the tampon into the vaginal canal is commonly achieved using a tampon applicator that comes initially assembled with the tampon. The applicator, which is often made of plastic or cardboard, is disposable. Thus, after the applicator has been used to insert the tampon into the user's vaginal canal the applicator is discarded.

Tampon applicators are typically of a two-piece construction, including a barrel in which the tampon is initially housed and a plunger moveable telescopically relative to the barrel to push the tampon out of the barrel and into the vaginal canal. The barrel has a tip that generally retains the tampon within the barrel until pushed through the tip by the plunger. In normal use, the applicator and more particularly the barrel of the applicator is held by the user by gripping one portion of the barrel (e.g., toward the trailing or plunger end of the barrel) and inserting the barrel, tip end first, into the vaginal canal. The barrel is pushed partially into the canal so that a portion (e.g., toward the leading or exit end of the tampon barrel) is disposed within the vaginal canal and is in contact with the walls lining the canal. The plunger is then used to push the tampon out through the tip of the barrel and into the canal. The plunger and barrel are then removed from the vaginal canal, leaving the tampon in place.

Typically, the plunger is flared at the end to provide comfort and control to the user during insertion of the applicator and expulsion of the tampon from the barrel. Frequently, the other end of the plunger is also flared to provide a broad surface to push against the tampon during expulsion. These flares also help to keep the plunger from separating from the barrel during insertion, expulsion, or while in the package.

Traditionally, one or both of these flared ends are formed in an operation separate from the molding of the plunger (i.e., a post production step). This separate operation usually occurs after assembly of the plunger and the barrel. While this method of assembling tampon applicators produces acceptable results, there is a need for a method to more efficiently assemble tampon applicator barrels and plungers with flared ends.

SUMMARY OF THE INVENTION

In response to this need, one aspect of the present invention provides a method of assembling a tampon applicator. The method includes the step of providing a barrel, wherein the barrel has an insertion end, a plunger end, and a plurality of internal ridges. The internal ridges define a guide channel having an effective diameter. The internal ridges have a leading end and a trailing end.

The method further includes the step of providing a plunger. The plunger has a finger-contacting end, a tampon-contacting end, and a flare on at least one of the finger-contacting end or the tampon-contacting end. The flare has an effective flare diameter that is greater than the effective diameter of the guide channel.

The method further includes the step of assembling the plunger and the barrel. The assembling includes pushing the flare into the guide channel, deforming the flare while moving the flare through the guide channel, and reestablishing the flare after the flare exits the guide channel.

In one embodiment of this aspect, the method may further include providing a plunger that includes a finger flare on the finger-contacting end wherein the finger flare has an effective finger flare diameter that is greater than the effective diameter of the guide channel. In these embodiments, the assembling step further includes the steps of moving the finger-contacting end of the plunger through the insertion end of the barrel and contacting the leading end of the plurality of internal ridges with the finger flare of the plunger. The assembling step further includes pushing the finger flare into the guide channel and deforming the finger flare while moving the finger flare through the guide channel. Finally, the assembling step further includes reestablishing the finger flare after the finger flare exits the guide channel.

In another embodiment of this aspect, the method may further include providing a plunger that includes a tampon flare on the tampon-contacting end wherein the tampon flare has an effective tampon flare diameter that is greater than the effective diameter of the guide channel. In these embodiments, the assembling step further includes the steps of moving the tampon-contacting end of the plunger through the plunger end of the barrel and contacting the trailing end of the plurality of internal ridges with the tampon flare of the plunger. The assembling step further includes pushing the tampon flare into the guide channel and deforming the tampon flare while moving the tampon flare through the guide channel. Finally, the assembling step further includes reestablishing the tampon flare after the tampon flare exits the guide channel.

In various embodiments, the effective flare diameter is at least 15% larger than the effective diameter of the guide channel.

In various embodiments, the barrel has three internal ridges.

In some embodiments, the barrel defines a circumference at the plunger end and has four internal ridges evenly spaced about the circumference.

In some embodiments, the plunger includes a hollow channel extending from the finger-contacting end to the tampon-contacting end. In these embodiments, the method may further include the step of inserting a tampon having a withdrawal string into the insertion end of the barrel after the assembly step and passing the withdrawal string through the hollow channel of the plunger.

In various embodiments, the finger flare has a circular shape before and after the assembling step and has a non-circular shape while moving through the guide channel.

In various embodiments, the insertion end of the barrel includes petals and the method further includes the step of bending the petals closed to substantially enclose the tampon within the barrel.

In various embodiments, the effective diameter of the guide channel as measured at the leading end of the ridges is greater than the effective diameter of the guide channel as measured at the trailing end of the ridges.

In another aspect, the present invention provides a method of assembling a tampon applicator. The method includes the step of providing a barrel wherein the barrel has an insertion end with petals, a plunger end, and a plurality of internal ridges. The internal ridges define a guide channel having an effective diameter and the internal ridges have a leading end and a trailing end.

The method further includes the step of providing a plunger wherein the plunger has a finger-contacting end, a tampon-contacting end, a finger flare on the finger-contacting end, and a tampon flare on the tampon-contacting end. The finger flare has a circular shape and has a flare diameter that is at least 15% larger than the effective diameter of the guide channel.

The method also includes the step of assembling the plunger and the barrel. The assembling step includes moving the finger-contacting end of the plunger through the insertion end of the barrel and contacting the leading end of the plurality of internal ridges with the finger flare of the plunger. The assembly step further includes pushing the finger flare into the guide channel and deforming the finger flare into a non-circular shape while moving the finger flare through the guide channel from the leading end of the internal ridges to the trailing end of the internal ridges. Finally, the assembly step includes moving the finger flare out of the plunger end of the barrel and reestablishing the circular shape of the finger flare.

The method also includes the step of inserting a tampon having a withdrawal string into the insertion end of the barrel after assembling the plunger and the barrel.

The method also includes the step of bending the petals closed to substantially enclose the tampon within the barrel.

In various embodiments of this aspect, the plunger includes a hollow channel extending from the finger-contacting end to the tampon-contacting end and the method further includes the step of passing the withdrawal string through the hollow channel of the plunger.

In various embodiments of this aspect, the barrel has a grip region, a central region, and a tip region. The grip region has a reduced diameter as compared to the central region and the ridges are located primarily in the grip region.

In various embodiments, the barrel has four internal ridges and each ridge has a ridge height of about 0.8 mm at the trailing end.

In various embodiments, the effective diameter of the guide channel as measured at the leading end of the ridges is greater than the effective diameter of the guide channel as measured at the trailing end of the ridges.

In some embodiments, the tampon flare has a flare diameter greater than the flare diameter of the finger flare.

In another aspect, the present invention provides a method of assembling a tampon applicator. The method includes the step of providing a barrel made of low density polyethylene. The barrel has an insertion end with petals, a plunger end, a grip region, a central region, and a tip region, and a plurality of internal ridges. The internal ridges define a guide channel having an effective diameter. The internal ridges have a leading end and a trailing end. The grip region has a reduced diameter as compared to the central region and the ridges are located primarily in the grip region.

The method of this aspect also includes the step of providing a plunger made of low density polyethylene. The plunger has a finger-contacting end, a tampon-contacting end, a finger flare on the finger-contacting end, a tampon flare on the tampon-contacting end, and a hollow channel extending from the finger-contacting end to the tampon-contacting end. The finger flare has a circular shape and has a flare diameter that is at least 15% larger than the effective diameter of the guide channel.

The method of this aspect also includes the step of assembling the plunger and the barrel. The assembling step includes moving the finger-contacting end of the plunger through the insertion end of the barrel and contacting the leading end of the plurality of internal ridges with the finger flare of the plunger. The assembling step also includes deforming the finger flare of the plunger into a non-circular shape while moving the finger flare from the leading end of the internal ridges to the trailing end of the internal ridges. Finally, the assembling step also includes moving the finger-contacting end of the plunger out of the plunger end of the barrel and reestablishing the circular shape of the finger flare.

The method of this aspect also includes the step of inserting a tampon having a withdrawal string into the insertion end of the barrel after assembling the plunger and the barrel. The method also includes passing the withdrawal string through the hollow channel of the plunger. Finally, the method of this aspect also includes bending the petals closed to substantially enclose the tampon within the barrel.

In various embodiments of this aspect, the barrel defines a circumference at the plunger end and has four internal ridges evenly spaced about the circumference.

In various embodiments of this aspect, the effective diameter of the guide channel as measured at the leading end of the ridges is greater than the effective diameter of the guide channel as measured at the trailing end of the ridges.

BRIEF DESCRIPTION OF THE DRAWINGS

Corresponding reference characters indicate corresponding parts throughout the drawings.

DETAILED DESCRIPTION OF THE DRAWINGS

Figure 1:
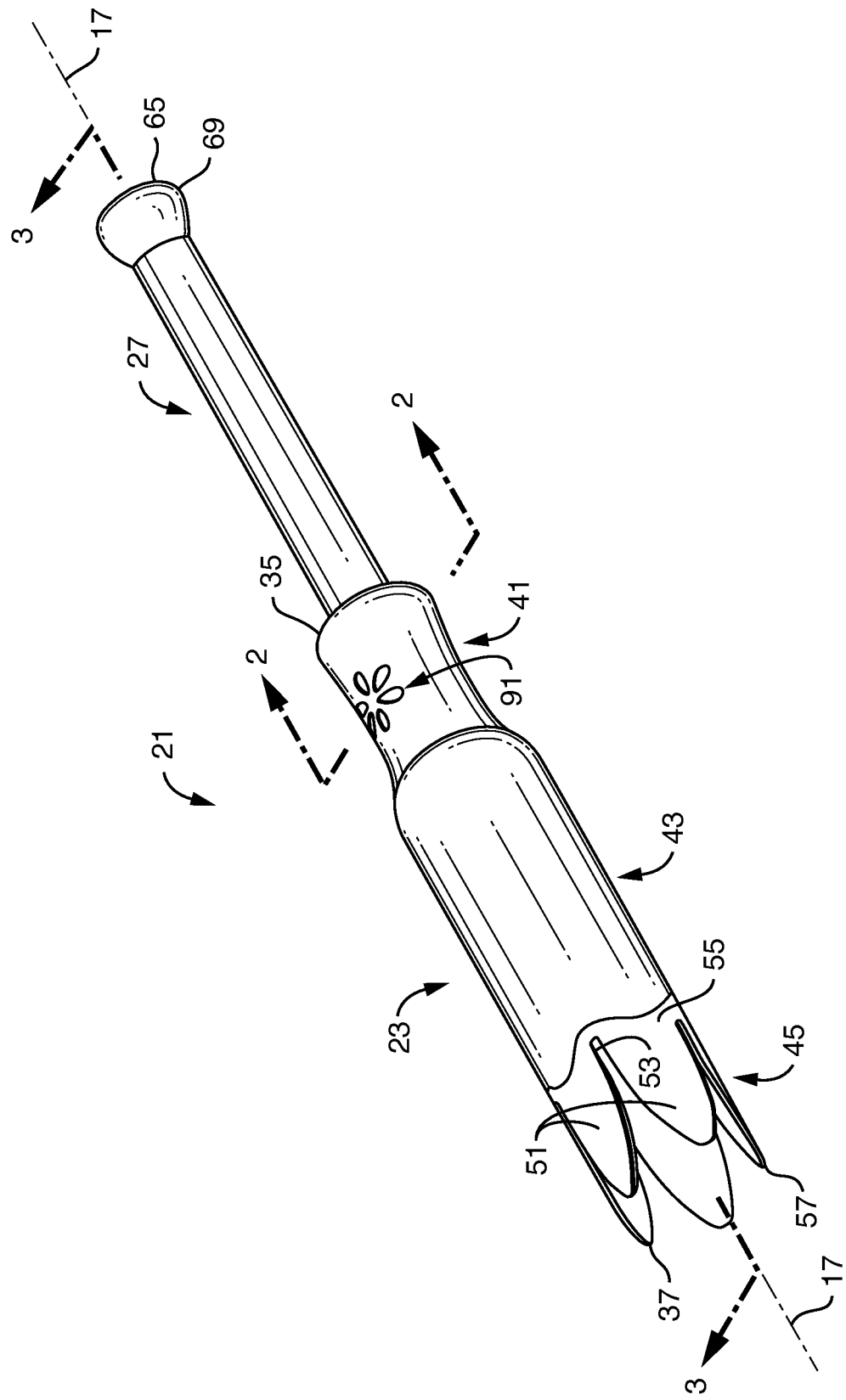
FIG. 1 is a perspective view of one embodiment of a tampon applicator with a plunger illustrated in an extended position relative to a barrel of the applicator and with a tip of the barrel open to illustrate construction of the barrel.

Referring now to the drawings and in particular to FIG. 1, one embodiment of a tampon applicator is generally designated by reference numeral 21. The tampon applicator comprises a barrel, indicated generally at 23, housing a tampon 25 (FIG. 6), and a plunger, indicated generally at 27, moveable telescopically relative to the barrel to expel the tampon from the barrel. In the various embodiments herein the tampon applicator 21 is illustrated and described in connection with a vaginal tampon 25, i.e., a tampon such as a fibrous body sized and shaped (typically cylindrically shaped) for insertion into the vaginal canal of a female user to absorb menses, blood and other bodily fluids. It is understood, however, that the applicators described herein may be used in connection with other vaginal inserts such as pessaries, diaphragms, medicants, and the like.

The tampon 25 includes a withdrawal string 29 (FIG. 6) fastened to the tampon generally adjacent an outer or trailing end 31 thereof for use in pulling the tampon from the vaginal canal. Suitable tampon 25 and withdrawal string 29 materials and constructions are known to those skilled in the art and are not further described herein except to the extent necessary to set forth the present invention.

The tampon applicator 21 has a longitudinal axis 17, with the barrel 23 and plunger 27 being in coaxial relationship with each other on this axis. The plunger 27 is thus moveable telescopically along the longitudinal axis 17 from an extended position as illustrated in FIG. 1 to a delivery position (not shown) to expel the tampon 25 from the barrel 23 of the applicator 21. It is understood, however, that the plunger 27 need not be coaxial with the barrel 23 and/or the longitudinal axis 17 of the applicator 21 to remain within the scope of this invention.

The barrel 23 of the tampon applicator 21 is suitably sized and shaped for housing the tampon 25 within an interior chamber 33 (FIGS. 3 and 6) of the barrel and for inserting the barrel into a body cavity of a user, such as the vaginal canal of a female user where the tampon is a vaginal tampon. The barrel 23 is generally elongated and also generally cylindrical, having an insertion end 37 and a plunger end 35. The barrel 23 also broadly comprises a grip region 41 adjacent the plunger end 35 of the barrel 23, a central region 43 longitudinally adjacent the grip region 41 and at least in part defining the interior chamber 33 housing the tampon 25, and a tip region 45 longitudinally adjacent the central region in longitudinally spaced relationship with the grip region 41. The terms insertion end 37 and plunger end 35 as used herein are referenced relative to the orientation of the tampon applicator 21 and its various components during use thereof, with the barrel 23 being inserted, insertion end 37 first, into the body cavity (e.g., the vaginal canal).

Figure 3:
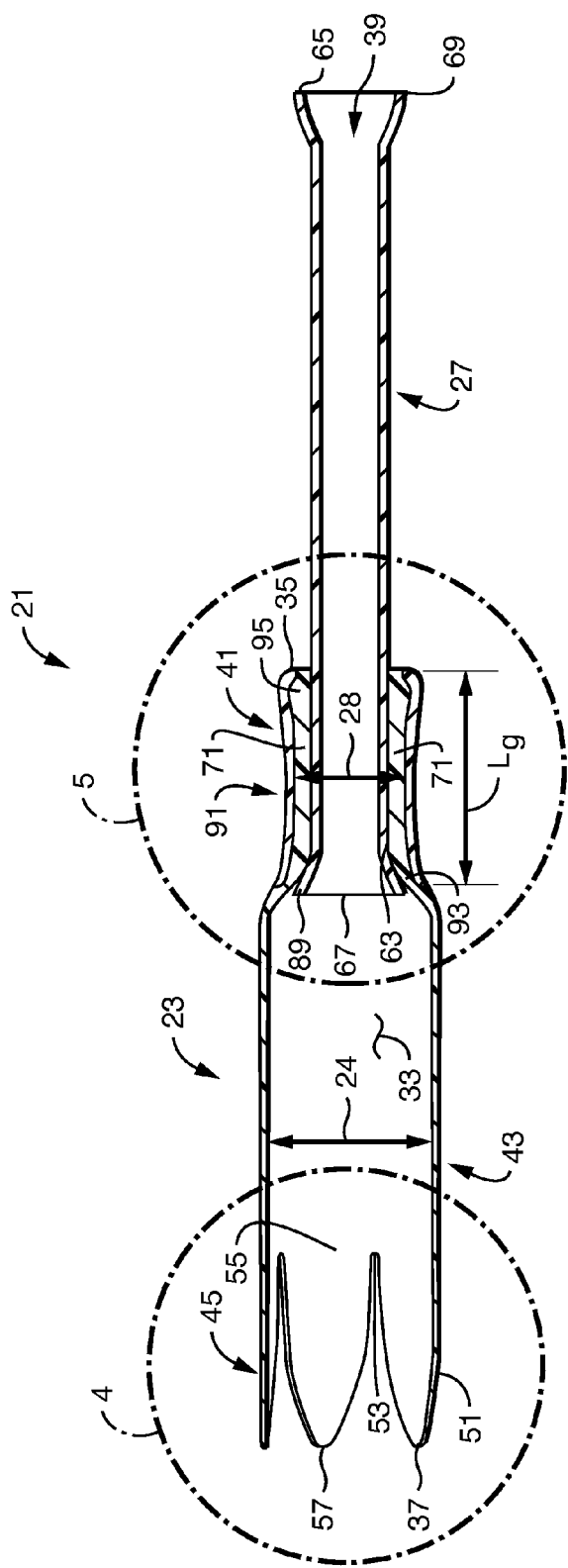
FIG. 3 is a longitudinal cross-section taken in the plane of line 3-3 of FIG. 1.
Figure 4:
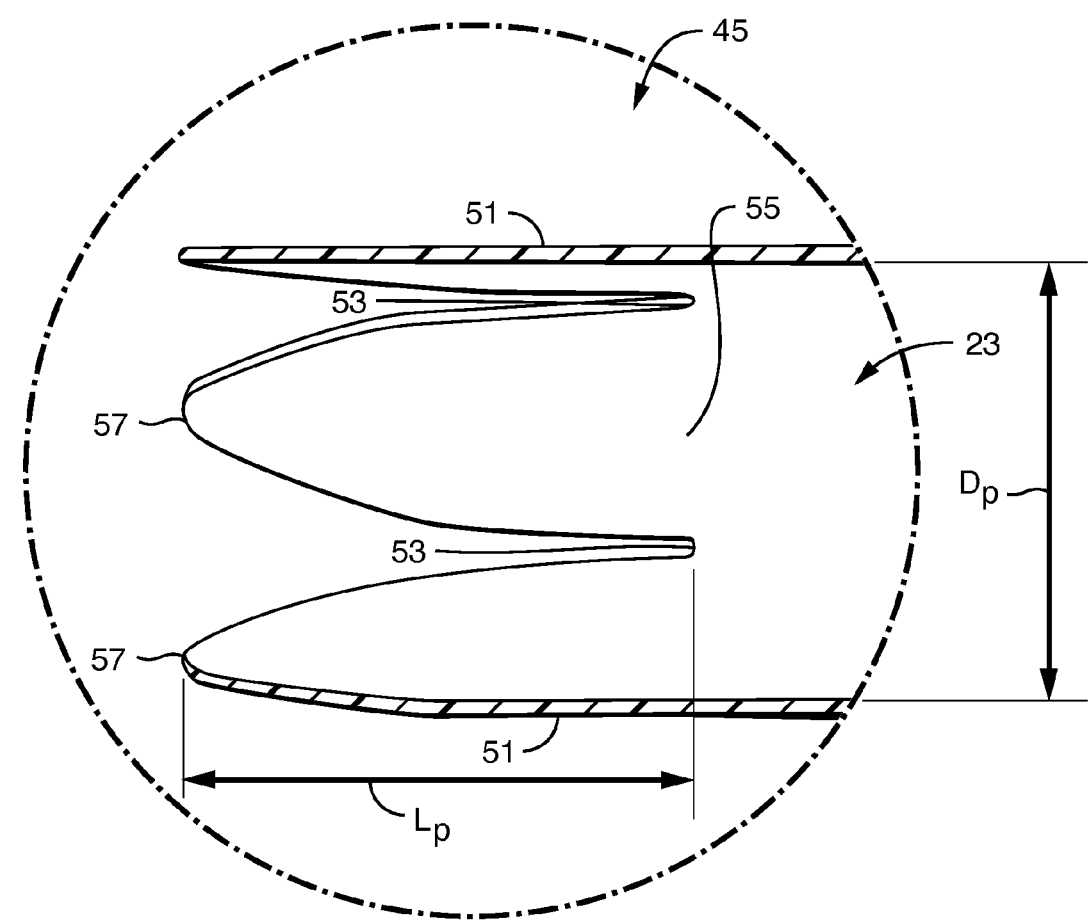
FIG. 4 is an enlarged view of a first longitudinal segment of the applicator of FIG. 3.
Figure 6:
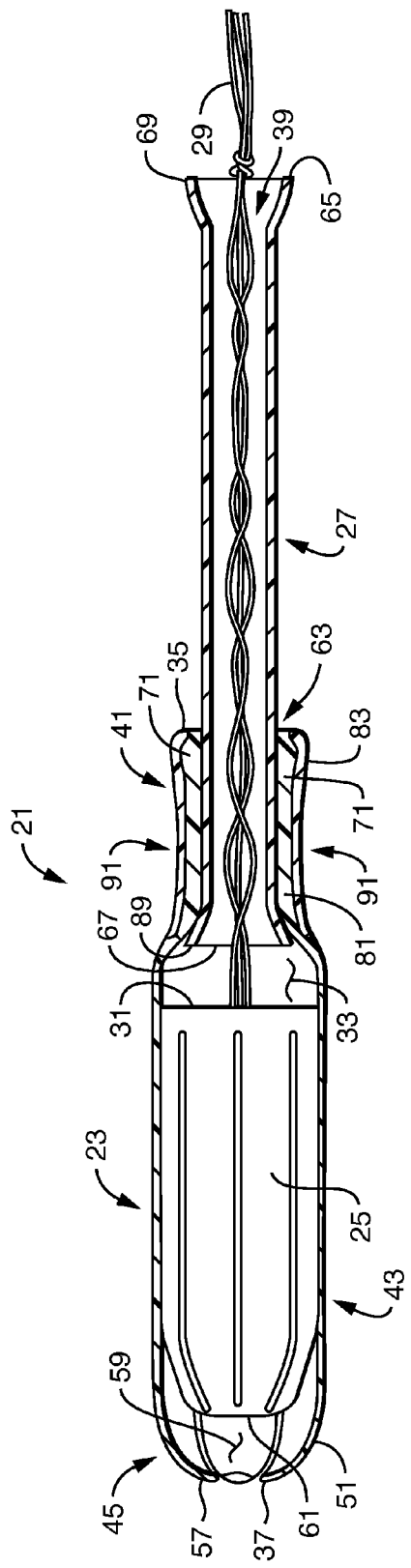
FIG. 6 is a longitudinal cross-section similar to FIG. 3 with a tampon included and the tip of the applicator barrel illustrated in its closed configuration.

With particular reference to FIGS. 3 and 4, the tip region 45 of the barrel 23 includes a plurality of extensions, or what is commonly referred to as petals 51, separated by longitudinal slots 53. Each of the petals 51 extends longitudinally from a base 55 of the petal 51, where the petal is connected to and is more suitably formed integrally with the rest of the barrel 23, to a free end or tip 57 of the petal. More suitably, the width of each petal tapers inward from its base 55 toward its tip 57. The petals 51 are suitably configured in this manner to permit the petals to be bent inward during manufacture of the applicator 21 as illustrated in FIG. 6 to generally close the barrel 23 at its insertion end 37 to substantially enclose the tampon 25 in the interior chamber 33 of the barrel during packaging and storage (e.g., prior to use). The slots 53 allow for bending of the petals 51 into their closed configuration during manufacture, and for flexing or bending transversely (e.g., radially in the illustrated embodiment) outward upon application of force by the tampon 25 when the tampon is guided out of the barrel 23 by the plunger 27.

The petals 51 may be sized in any suitable length $L_p$, e.g., as measured from the base 55 of the petal to its longitudinally furthest extent such as the tip 57 in FIG. 4. The petals 51 may be sized so that the petals are more readily flexed or bent transversely outward from their closed configuration to allow easier expulsion of the tampon 25 from the barrel 23 and to reduce the occurrences and strength of the petals pinching the user. For example, in one embodiment the length $L_p$ of each petal 51 is in the range of about 10 mm to about 20 mm and is more suitably about 16 mm. In another embodiment, the applicator barrel 23 has an inner diameter $D_p$ at the bases 55 of the petals 51, with the length $L_p$ of the petals being at least equal to and more suitably greater than the inner diameter of the applicator barrel at the bases of the petals. For example, in a particularly suitable embodiment a ratio of the petal length $L_p$ to the inner diameter $D_p$ of the barrel 23 at the base 55 of the petals 51 is in the range of about 1.0 to about 2.0, more suitably in the range of about 1.0 to about 1.5, even more suitably in the range of about 1.0 to about 1.25, and most suitably about 1.1. As another example, in the illustrated embodiment the barrel 23 has an inner diameter $D_p$ of about 14.5 mm at the bases 55 of the petals, and a petal length of about 15.8 mm, which provides a petal length to inner diameter ratio of about 1.1.

Such a configuration allows the petals 51 to be bent inward to their closed configuration closer to the tips 57 of the petals, such as approximately the longitudinally outer one-third of each petal, as opposed to being bent nearer to or at their bases 55. This provides a softer and more flexible feel to the petals 51 in their closed configuration and also facilitates the formation of a gap 59 (FIG. 6) longitudinally between an insertion end 61 of the tampon 25 and the tips 57 of the petals when the petals are in their closed configuration (in which the tips of the petals broadly define the insertion end 37 of the barrel 23). For example, in some embodiments the gap 59 between the inner end 61 of the tampon 25 and the insertion end 37 of the barrel is in the range of about 0.1 mm to about 1.5 mm, about 0.1 mm to about 0.75 mm, or about 0.1 mm to about 0.4 mm. However, in some embodiments, the gap 59 may be up to about 4 mm. The portions of the petals 51 that form this gap 59 are thus more compressible and flexible (e.g., because of the lack of support or stiffness that would otherwise be provided by the tampon 25 absent such a gap), thereby enhancing the soft and flexible feeling of the tip region 45 of the barrel 23. It is understood, however, that the petals 51 at the tip region 45 of the barrel 23 may be sized other than as described above, including being sized so that no gap 59 is present, without departing from the scope of this invention.

In some embodiments, to further facilitate a more soft and flexible feel and appearance at the tip region 45, the petals 51 are configured to have a lower stiffness (i.e., resistance to bending) than the central region 43 of the barrel. More suitably, the petals 51 may be formed to have a thickness that is less than the thickness of the barrel 23 at the central region 43 to effect a lower stiffness. For example, the petals may have a thickness in the range of about 0.2 mm to about 0.8 mm while at the central region 43 the barrel may have a thickness of about 0.4 mm to about 1.2 mm. The reduced thickness of the petals 51 allows the petals to be more flexible and pliable to provide a soft, flexible feel and appearance. It is understood, however, that the thickness of the petals 51 and/or the central region 43 of the barrel 23 may be other than as set forth above.

Figure 2:
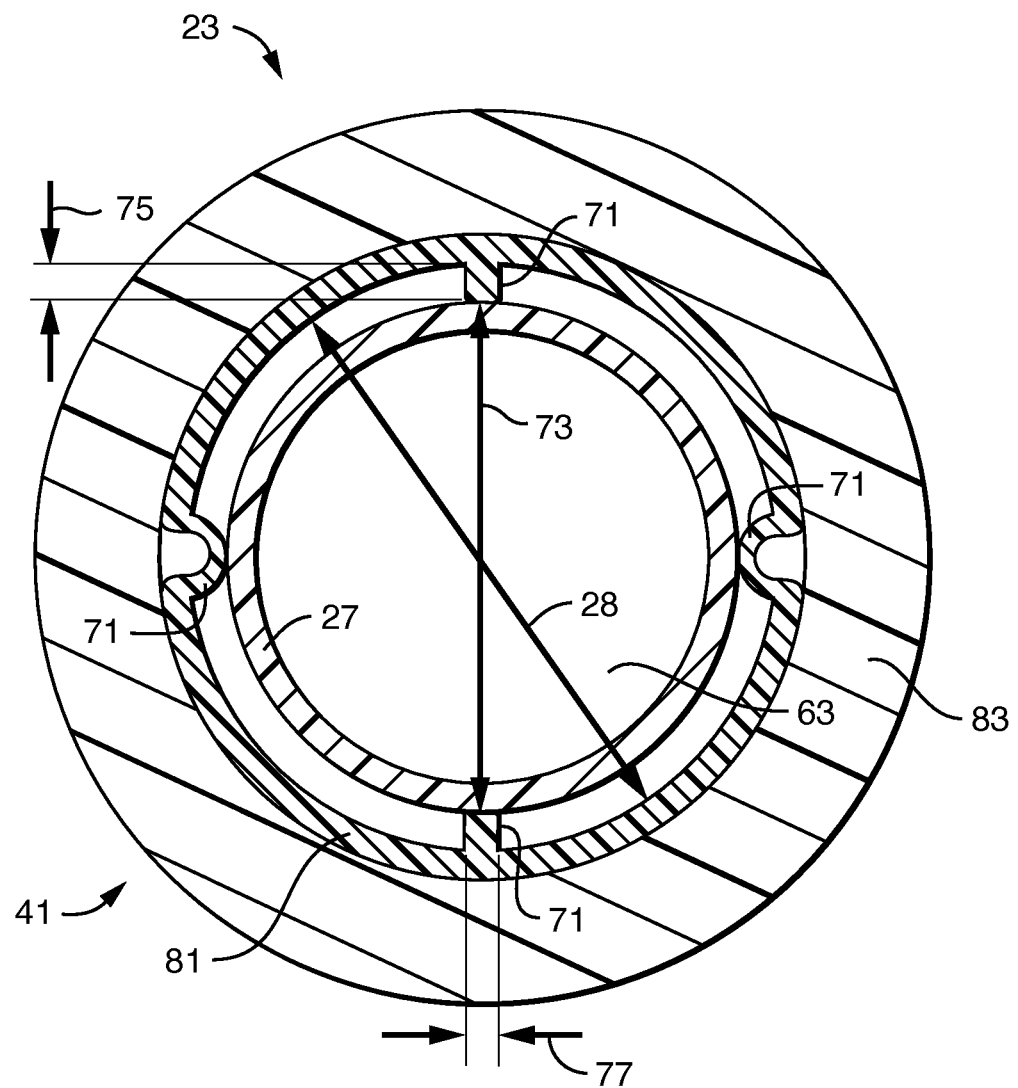
FIG. 2 is a transverse cross-section taken in the plane of line 2-2 of FIG. 1.

With reference to FIGS. 2 and 3, the barrel 23 has an inner diameter 28 proximate the plunger end 35 (e.g., at and/or adjacent the grip region 41) of the barrel 23. Likewise, the barrel 23 has an inner diameter 24 along the central region 43 of the barrel 23 (i.e., the portion that at least in part defines the interior chamber 33 in which the tampon 25 is housed).

The inner diameter 28 of the grip region 41 may be substantially less than the inner diameter 24 along the central region 43 of the barrel 23 as illustrated in FIG. 3. However, in some embodiments, the inner diameter 28 of the grip region 41 may be approximately the same size as the inner diameter 24 along the central region 43 of the barrel 23 (not illustrated) or may be larger than the inner diameter 24 along the central region 43 of the barrel 23 (not illustrated). In specific embodiments, the inner diameter 24 along the central region 43 may be about 12 to 17 mm or about 13.5 mm-14.5 mm. Likewise, the inner diameter 28 of the grip region 41 may be about 6 to 10 mm or about 8 mm.

Figure 5:
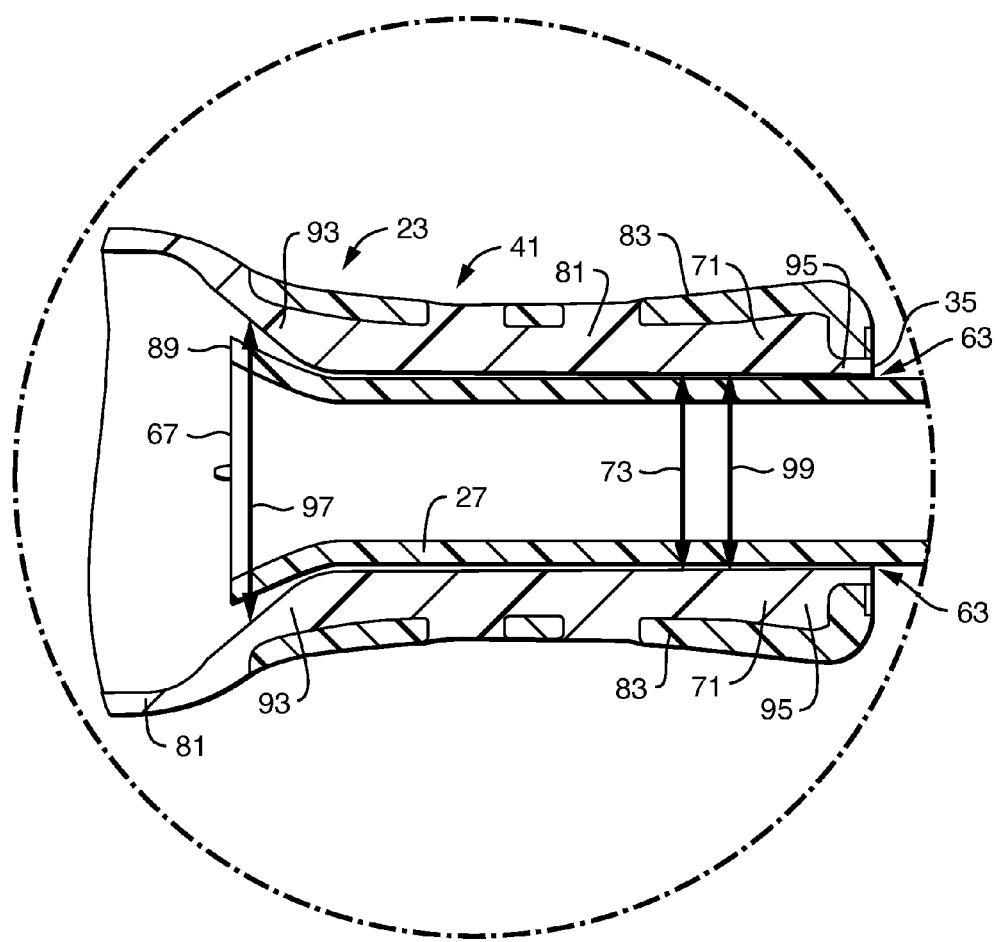
FIG. 5 is an enlarged view of a second longitudinal segment of the applicator of FIG. 3.
Figure 8:
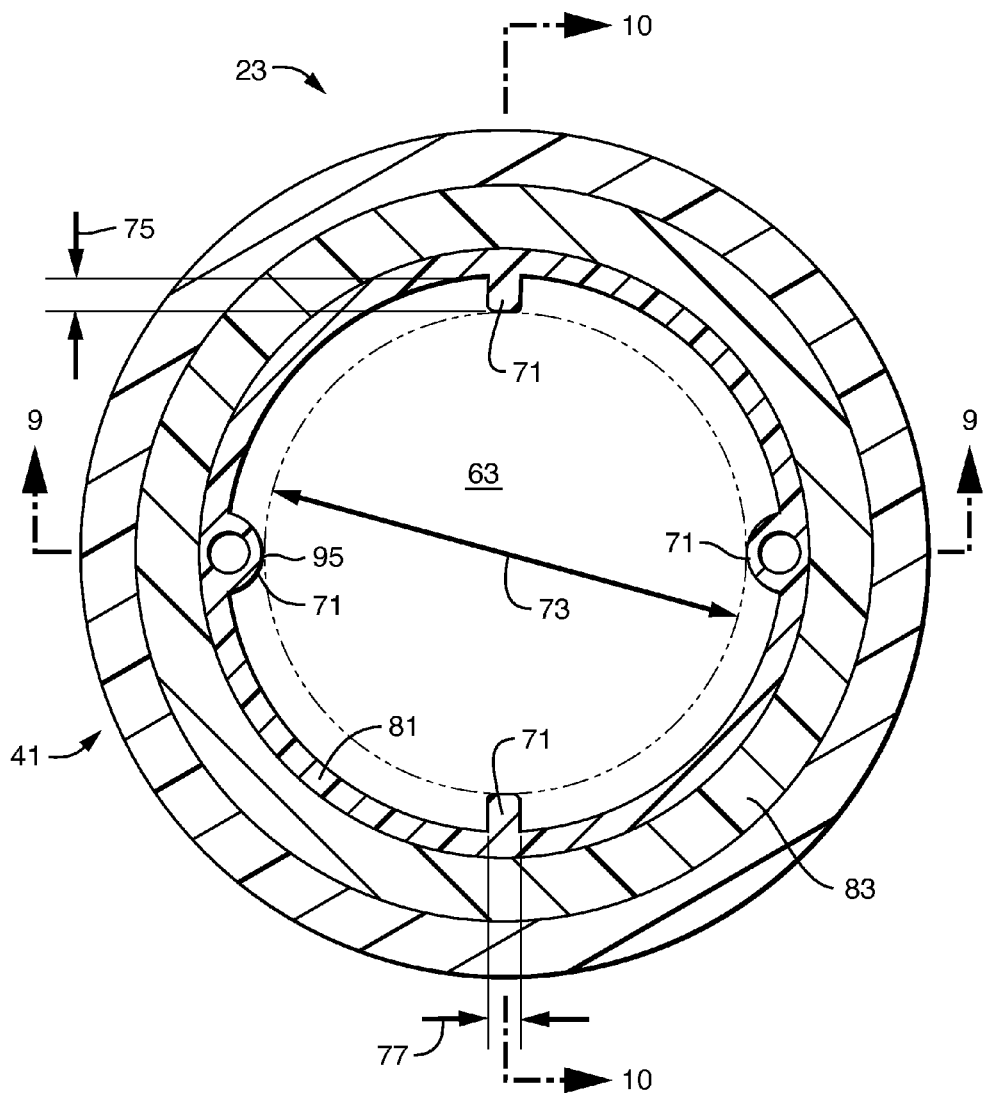
FIG. 8 is an end view of the barrel of FIG. 7.

The barrel 23 also includes a plurality of internal ridges 71 as illustrated, for example, in FIGS. 2 and 3. In various embodiments, the internal ridges 71 may be located in the grip region 41 or the central region 43 or a combination of both the grip region 41 and the central region 43. For example, as illustrated in FIGS. 3 and 6, the internal ridges 71 are located primarily in the grip region 41. The ridges 71 extend into the barrel 23 to provide support and alignment of the plunger 27 as it moves through the barrel 23. Specifically, the ridges 71 collectively define a longitudinal guide channel 63 through which the plunger 27 extends and is supported by ridges 71 in coaxial (or at least longitudinal) relationship with the barrel 23 as illustrated in FIGS. 2, 3, and 5. The ridges 71 define an effective diameter 73 sized for a sliding friction fit with the plunger 27. The effective diameter 73 is the diameter of the guide channel 63 defined by the inner surfaces of the ridges 71 as illustrated in FIGS. 2 and 8.

Figure 24:
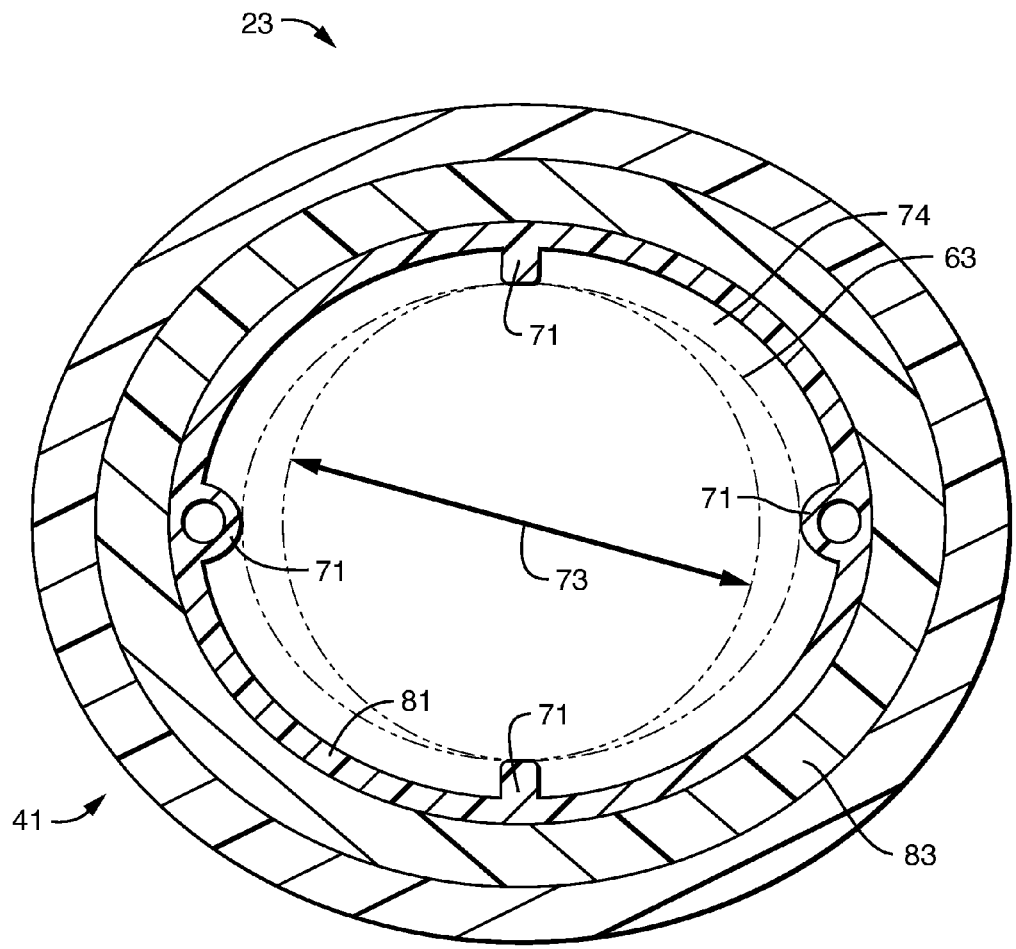
FIG. 24 is an end view of a barrel having a non-circular guide channel.

In embodiments wherein the guide channel 63 is non-circular, the effective diameter 73 is the diameter of the largest cylinder that could pass through the guide channel 63 without deformation. For example, referring now to FIG. 24, a non-circular guide channel 63 is illustrated. Specifically, FIG. 24 representatively illustrates an end view of an exemplary barrel 23 as viewed from the plunger end 35. The barrel 23 of FIG. 24 includes ridges 71 extending into the barrel 23 to provide support and alignment of a plunger (not illustrated). The ridges 71 define a guide channel 63 having a generally oval shape and an effective diameter 73.

The ridges 71 define a leading end 93 and a trailing end 95 as illustrated in FIGS. 3 and 5. The leading end 93 is oriented towards the insertion end 37 of the applicator 21 and the trailing end 95 is oriented towards the plunger end 35 of the applicator 21. In various embodiments, the effective diameter 73 may be the same from the leading end 93 to the trailing end 95. However, in some embodiments, the effective diameter 73 may vary from the leading end 93 to the trailing end 95. For example, as illustrated in FIG. 5, the internal ridges 71 may define a first effective diameter 97 proximate the leading end 93 of the ridges 71 and a second effective diameter 99 proximate the trailing end 95 of the ridges 71.

In various embodiments, the first effective diameter 97 may be greater than the second effective diameter 99 as illustrated in FIG. 5. However, it will be readily appreciated that in some embodiments, the second effective diameter 99 proximate the trailing end 95 may be greater than the first effective diameter 97 proximate the leading end 93 (not illustrated). In specific embodiments, the first effective diameter 97 as measured proximate the leading end 93 may be about 8 to 12 mm or about 9.5 mm and the second effective diameter 99 as measured proximate the trailing end 95 may be about 5-7 mm or about 6.35 mm as measured at the narrowest point. In some embodiments, the effective diameter 73 of the guide channel 63 may gradually decrease from the leading end 93 to the trailing end 95 as illustrated in FIG. 5. In other embodiments, the effective diameter 73 of the guide channel 63 may gradually decrease from the trailing end 95 to the leading end 93 (not illustrated). The graduated changes in effective diameter may be selected to aid in assembly of the tampon applicator as described herein.

Figure 7:
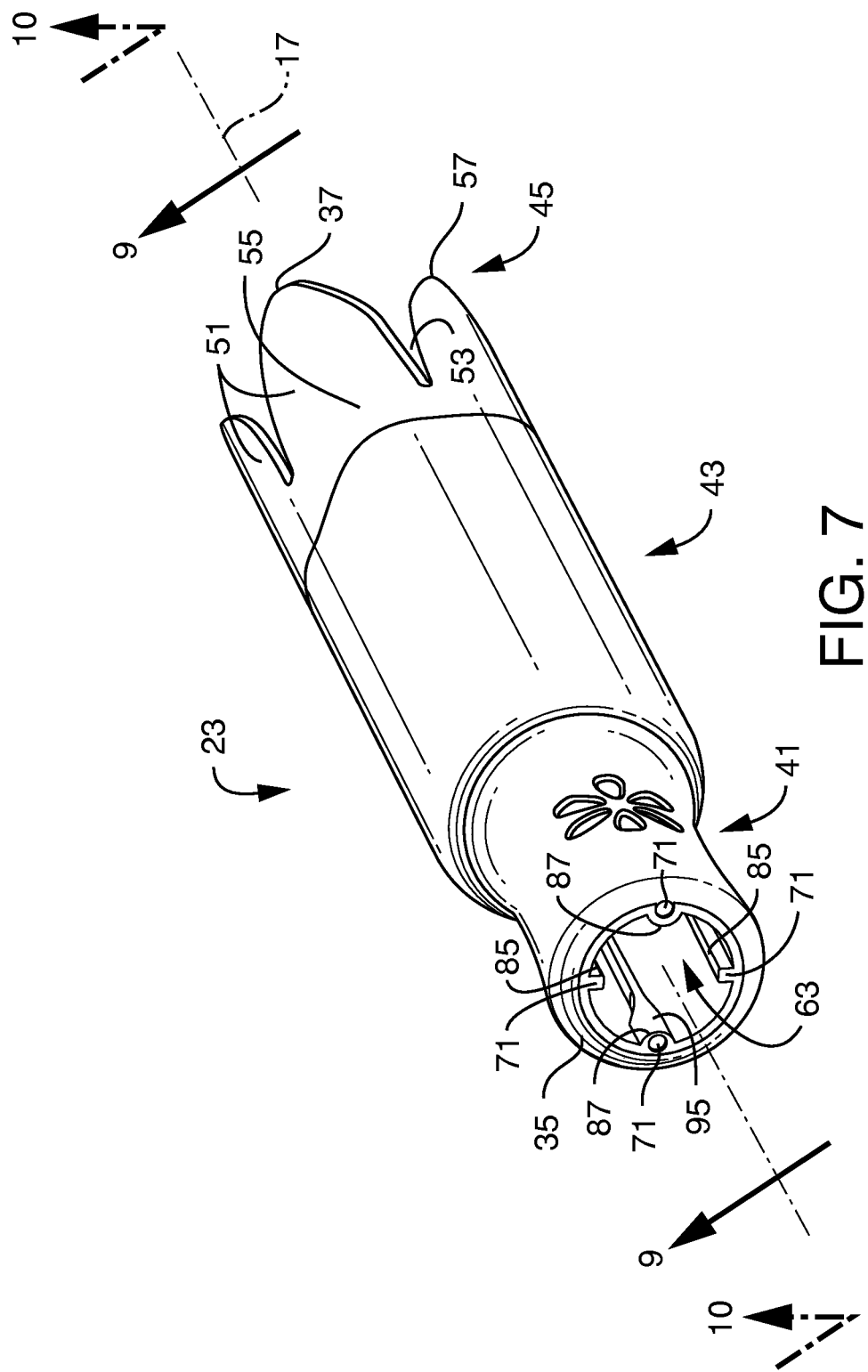
FIG. 7 is a perspective view of one embodiment of a tampon applicator barrel without a plunger.
Figure 9:
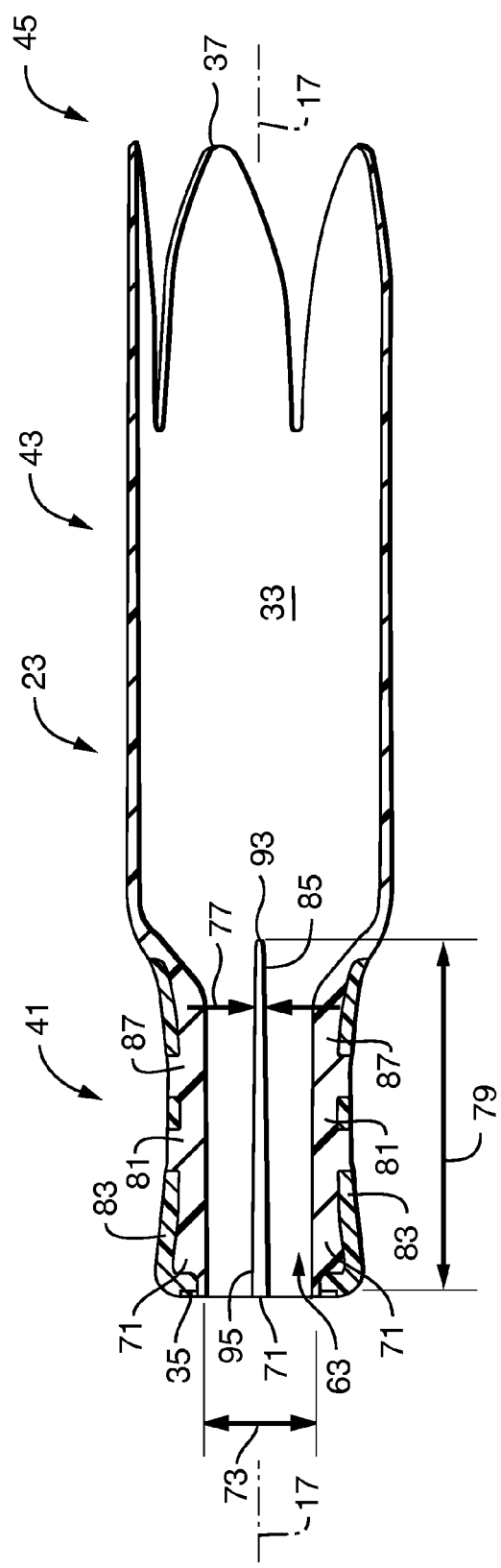
FIG. 9 is a longitudinal cross-section taken in the plane of line 9-9 of FIGS. 7 and 8.
Figure 10:
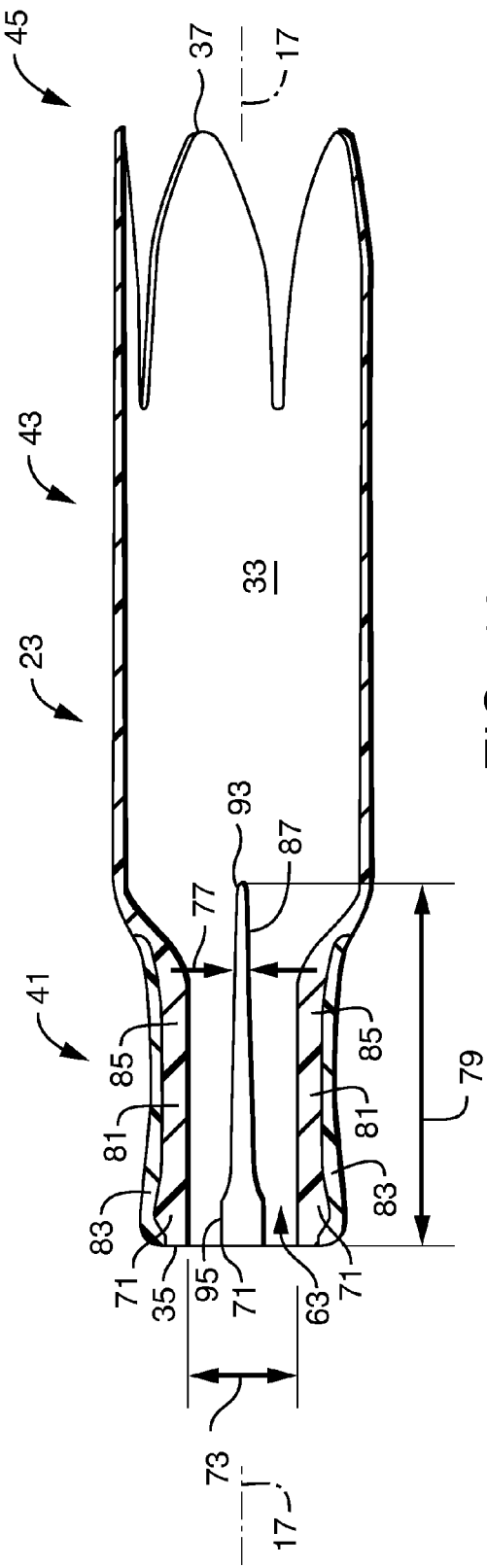
FIG. 10 is a longitudinal cross-section taken in the plane of line 10-10 of FIGS. 7 and 8.

Referring now to FIGS. 7-10 an exemplary barrel 23 of the present invention is illustrated. Specifically, FIG. 7 is a perspective view of one embodiment of a tampon applicator barrel 23 without a plunger. FIG. 8 is an end view of the barrel of FIG. 7 whereas FIGS. 9 and 10 are longitudinal cross-sections taken in the planes of lines 9-9 and 10-10 respectively. The ridges 71 may have any suitable height 75, width 77, length 79, or cross-sectional shape. In various embodiments, the ridges 71 may have a ridge height 75 as illustrated in FIG. 8. The ridge height 75 may be constant or may vary along the longitudinal direction. For example, the ridge height 75 may vary from about 0.8 mm at the plunger end 35 to about 0.9 mm at the transition region between the grip region 41 and the central region 43.

In various embodiments, the ridges 71 may have a ridge width 77 as illustrated in FIGS. 9 and 10. The ridge width 77 may be constant or may vary along the longitudinal direction 17. For example, the ridge width 77 may vary from about 0.8-2.0 mm at the trailing end 95 of the ridge 71 to about 0.5 mm at the leading end 93 of the ridge 71 as illustrated in FIGS. 9 and 10.

In various embodiments, the ridges 71 may have a ridge length 79 as illustrated in FIGS. 9 and 10. The ridge length 79 may be any suitable distance to provide the desired plunger stability. For example, the ridge length 79 may be about 15-25 mm or about 22 mm.

In various embodiments, the ridges 71 may have any suitable cross-sectional shape. For example, the ridges 71 may have a cross-sectional shape that is generally circular, triangular, ovular, hemispherical, rectangular, or the like or combinations thereof. For example, FIGS. 7-10 illustrate ridges 87 having a generally hemispherical cross-sectional shape proximate the trailing end 95 and a generally rectangular or triangular cross-sectional shape proximate the leading end 93. Likewise, FIGS. 7-10 illustrate other ridges 85 having a generally rectangular cross-sectional shape proximate the trailing end 95 and a generally rectangular or triangular cross-sectional shape proximate the leading end 93. In various embodiments, the ridges 71 may be all the same in shape and/or size or may be different in shape or size. For example, FIGS. 7-10 illustrate two ridges 85 having a first shape and two ridges 87 having a second shape that is at least partially different than the first shape.

Ridge height 75, ridge width 77, and the number of ridges 71 can be adjusted to provide adequate deformation space 74 (FIG. 14) such that the flares may be deformed during assembly using a suitable force as discussed herein. For example, if the ridge height 75 is relatively small, the deformation space 74 will be relatively small. Likewise, the number of ridges 71 is inversely proportional to the deformation space 74 available to receive portions of the deformed bell.

In various embodiments, any suitable number of ridges 71 may be employed. For example, the tampon applicator 21 may have 1-6 ridges. However, it is believed that 3-5 ridges 71 provide a good balance of plunger deformation during assembly and plunger stability during use. In some embodiments, 4 ridges 71 are preferred as illustrated in FIG. 7. The ridges 71 may be spaced in any suitable manner. In some embodiments, the ridges 71 may be spaced evenly about the circumference of the barrel 23 as illustrated in FIGS. 7 and 8.

In various embodiments, the ridges 71 may be essentially linear and may be oriented parallel with the longitudinal direction of the tampon applicator 21 as illustrated herein. In other embodiments, one or more of the ridges 71 may be non-linear and/or may be non-parallel with the longitudinal direction. For example, the ridges may spiral within the barrel (not illustrated).

The plunger 27 is elongated and may include a hollow channel 39 (FIGS. 3 and 6) so that the withdrawal string 29 attached to the tampon 25 can extend out through the finger-contacting end 65 of the plunger. It is understood though that the plunger 27 need not include a hollow channel 39, and that the withdrawal string 29 may extend other than through the plunger without departing from the scope of this invention. A substantial length of the plunger 27, extending to the finger-contacting end 65 thereof, is accessible exterior of the barrel 23 in the extended position of the plunger for gripping by the user to move the plunger relative the barrel. The plunger has an increased outer diameter adjacent its finger-contacting end 65, such as in the form of a finger flare 69. The finger flare 69 may take any suitable shape such as a flange, ring, or bell-shape as in the illustrated embodiment or other suitable shape to facilitate gripping and/or pushing the plunger and to act as a stop to inhibit the finger-contacting end 65 of the plunger 27 against entering the barrel 23. Likewise, the plunger 27 may have an increased outer diameter adjacent its tampon-contacting end 67, such as in the form of a tampon flare 89. The tampon flare 89 may take any suitable shape such as a flange, ring, or bell-shape as in the illustrated embodiment or other suitable shape to facilitate pushing against the tampon 25 and to act as a stop to inhibit the tampon-contacting end 67 of the plunger 27 against exiting the barrel 23.

Figure 11:
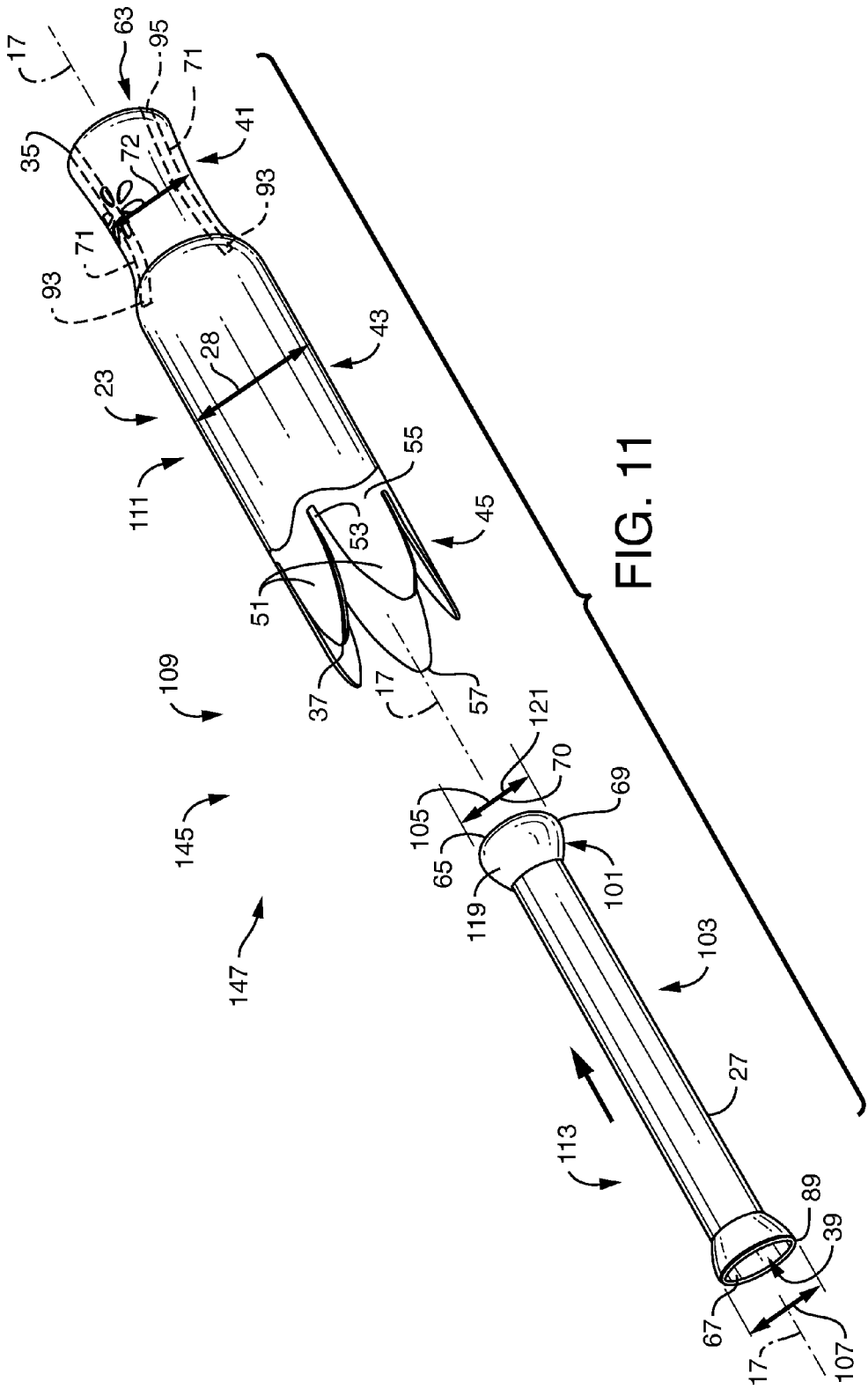
FIG. 11 is a perspective view of the first steps in a first method for assembling the tampon applicator of FIG. 1.
Figure 22:
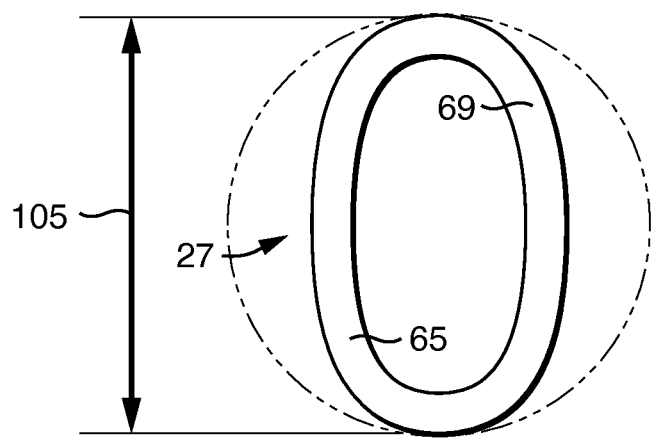
FIG. 22 is an end view of a non-circular finger flare.
Figure 23:
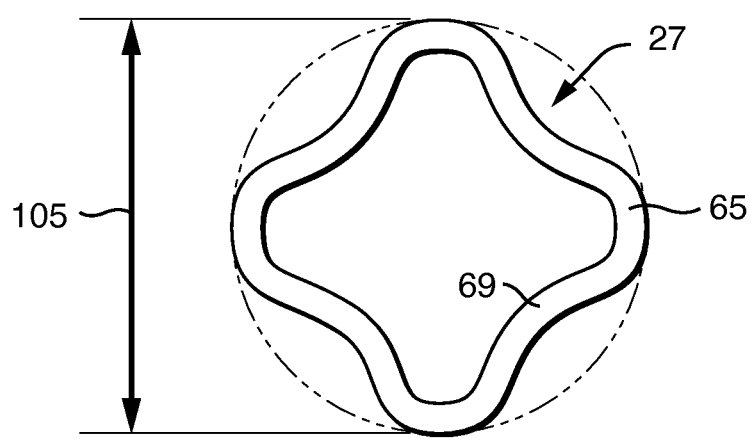
FIG. 23 is an end view of another non-circular finger flare.

Referring now to FIG. 11, the finger flare 69 may have any suitable effective diameter 105 and the tampon flare 89 may have any suitable effective diameter 107. As used herein, the term "effective diameter" is equivalent to the outer diameter of flares having a circular shape. For flares having a non-circular shape, the term "effective diameter" refers to the diameter of the smallest cylinder through which the non-circular flare can pass without deformation. For example, FIGS. 22 and 23 illustrate end views of exemplary plungers 27 having finger-contacting ends 65 having non-circular finger flares 69 and the corresponding effective diameter 105.

In various embodiments, the finger flare 69 may be any suitable diameter greater than the effective diameter 73 of the guide channel 63. For example, the finger flare 69 may have an effective diameter 105 of at least 5 mm, at least 6 mm, at least 7 mm, or at least 8 mm and is greater than the effective diameter 73 of the guide channel 63. In specific embodiments, the finger flare 69 may have an effective diameter of about 7.43 mm. In various embodiments, the finger flare 69 may have an effective diameter 105 that is at least 5%, at least 10%, at least 15%, or at least 20% larger than the effective diameter 73 of the guide channel 63.

In various embodiments, the tampon flare 89 may be any suitable diameter greater than the effective diameter 73 of the guide channel 63. For example, the tampon flare 89 may have an effective diameter 107 of at least 5 mm, at least 6 mm, at least 7 mm, at least 8 mm, or at least 9 mm and is greater than the effective diameter 73 of the guide channel 63. In specific embodiments, the tampon flare 89 may have an effective diameter of about 9.3 mm. In various embodiments, the tampon flare 89 may have an effective diameter 107 that is at least 5%, at least 10%, at least 15%, or at least 20% larger than the effective diameter 73 of the guide channel.

The plunger 27 may have any suitable wall thickness. For example, the plunger 27 may have a uniform wall thickness along its entire length or may have a variable wall thickness along its length. For example, in one embodiment, the plunger 27 may have a finger flare portion 101 having a wall thickness of 0.57 mm and may have a shaft portion 103 having a wall thickness of 0.64 mm (FIG. 11).

In various embodiments, the barrel 23 may be constructed such that all or some of the outer surface has any suitable coefficient of friction to facilitate comfortable insertion of the barrel into the vaginal canal and removal therefrom as disclosed in greater detail in U.S. Publication 2010/0016780 (application Ser. No. 12/173,516) to VanDenBogart, the entirety of which is incorporated herein by reference where not contradictory. In one example, the barrel 23 may be suitably constructed of at least two materials that differ in at least one characteristic. More suitably, in one embodiment the barrel is constructed of a first material that comprises the tip region 45, central region 43 and an underlying portion of the grip region 41, and a second material that comprises the overlying portion of the grip region. For example, the barrel 23 may be constructed along its full length (i.e., at the tip region 45, central region 43 and grip region 41) of a polymeric first or core layer 81 (FIGS. 2 and 5) comprising a polyolefin such as, without limitation, polypropylene, polyethylene, low density polyethylene, medium density polyethylene, high density polyethylene, linear low density polyethylene, near low density polyethylene, polyethylene terephthalate PET), nylon, polystyrene, polyvinyl chloride, polymethyl methacrylate, polyolefin elastomer, copolymers of alfa-olefines, and combinations thereof. More suitably the first or core layer 81 of the barrel 23 is formed of a low density polyethylene or a polymeric blend that includes low density polyethylene, such as a combination of low density polyethylene and at least one of linear low density polyethylene or a high density polyethylene.

One or more additives may be added to the polymeric first layer 81 of the barrel 23 (prior to molding) to enhance the slip characteristic (e.g., to provide a low coefficient of friction) of the barrel outer surface at least at the central region 43 of the barrel and more suitably at the central region and tip region 45 of the barrel. For example, suitable such additives include without limitation erucamide, demethicone, oleamide, fatty acid amide and combinations thereof. It is understood that other additives may be used to provide enhanced slip characteristics to the barrel 23 outer surface without departing from the scope of this invention. In other embodiments the barrel 23 may instead, or additionally, be coated with a friction reducing, or slip agent such as, without limitation, wax, polyethylene, silicone, cellophane, clay and combinations thereof. In still other suitable embodiments, the barrel 23 may comprise a polymer blend melted together and co-extruded to provide a low coefficient of friction.

In the illustrated embodiment, the barrel 23 is further constructed so that the barrel outer surface at the tip region 45 has a lower coefficient of friction than at the central region 43 of the barrel to facilitate easier insertion of the barrel, inner end first, into the vaginal canal. This is particularly useful on days which a period is relatively light. For example, the outer surface of the barrel 23 at the tip region 45 may be configured to have a substantially lower surface roughness than at the central region 43 of the barrel, and more suitably the tip region may be substantially smooth or polished to reduce the coefficient of friction of the tip region relative to that of the central region.

In another embodiment, the first or core layer 81 is constructed of at least two different but generally compatible materials (e.g., so that the barrel 23 is comprised of at least three materials—including the material from which the grip region 41 is constructed). In one particular such embodiment, the central region 43 and the tip region 45 of the barrel 23 are of different materials. The material from which the central region 43 is formed may also form an underlying layer of the grip region 41 and a third material forms an overlying or outer layer of the grip region. As an example, one suitable process for making the first or core layer 81 of at least two different materials as described above is referred to as a coinjection process and more particularly a sequential coinjection process. Such injection processes are known to those skilled in the art for molding together two compatible polymer melts.

In other embodiments, the tip region 45 of the barrel 23 may instead, or additionally, be coated with a friction reducing agent so that the outer surface of the barrel at the tip region has a lower coefficient of friction than that of the central region of the barrel. Providing a surface roughness differential between the tip region 45 and the central region 43 also serves as a visual indicator of the reduced friction coefficient at the tip region.

The grip region 41 is suitably constructed of a second or skin layer 83 applied over the first or core layer 81 along a longitudinal segment of the barrel 23 generally at the grip region thereof. In one particularly suitable embodiment, the second, or skin layer 83 forming the grip region 41 may comprise a thermoplastic elastomer (TPE) to provide the grip region with a soft, relatively rubbery feel that has a higher coefficient of friction than the first or core layer 81 that defines the outer surface of at least the central region 43 of the barrel 23. It is understood, however, that other suitable materials may be used as the second or skin layer 83 to provide a higher coefficient of friction to the grip region 41 without departing from the scope of this invention.

In the illustrated embodiment of FIG. 1, a visual indicator, indicated generally at 91, is provided at the grip region 41 to facilitate identification by the user of the grip region location. The visual indicator 91 in FIG. 1, for example, comprises a flower pattern formed in the grip region 41 to identify the grip region. More particularly, an underlying set of flower petals is formed as part of the first or core layer 81 of the barrel 23 during molding. The second or skin layer 83 of the barrel 23 at the grip region 41 has openings therein corresponding to and aligned with the molded flower petals so that the flower petals are visually perceptible through the second or skin layer of the barrel. More suitably, the flower petals are of a different color (such as by being the same color as the central region 43 of the barrel 23) than the second or skin layer 83 that defines the grip region 41.

It is understood that the visual indicator 91 may be formed other than integrally with the barrel 23 during initial molding of the barrel, such as by imprinting the visual indicator on the barrel at the grip region (e.g., a textual message or a suitable image) without departing from the scope of this invention. It is also understood that a visual indicator 91 (other than the different material and/or color of the second or skin layer 83) may be omitted from the grip region 41.

The applicator plunger 27 is, in one particularly suitable embodiment, constructed of the same material (e.g., polymer or polymer blend) as at least the first layer 81 (FIG. 2, e.g., the central region 43 and/or tip region 45) of the barrel to provide a relatively low coefficient of friction to the plunger for sliding within the guide channel 63. While not shown in the drawings, it is contemplated that the plunger 27 may also be formed by a coinjection process similar to that used to form the barrel 23 so that a second or skin layer is applied to the plunger, such as at or adjacent the finger-contacting end 65 of the plunger to facilitate enhanced gripping of the plunger during use. It is also contemplated that the end of the plunger 27 may be constructed to have a relatively smooth or polished outer surface and as such have a different surface roughness and/or visual appearance than the rest of the plunger.

Figure 12:
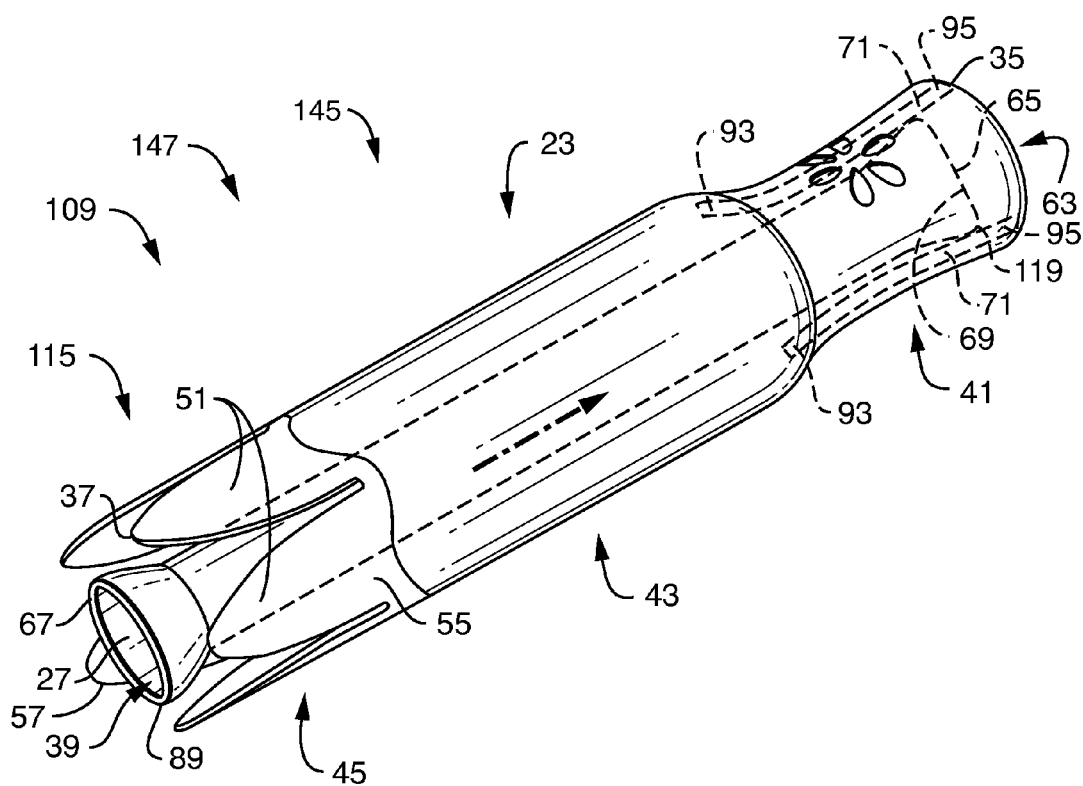
FIG. 12 is a perspective view of another step in the first method for assembling the tampon applicator of FIG. 1.
Figure 13:
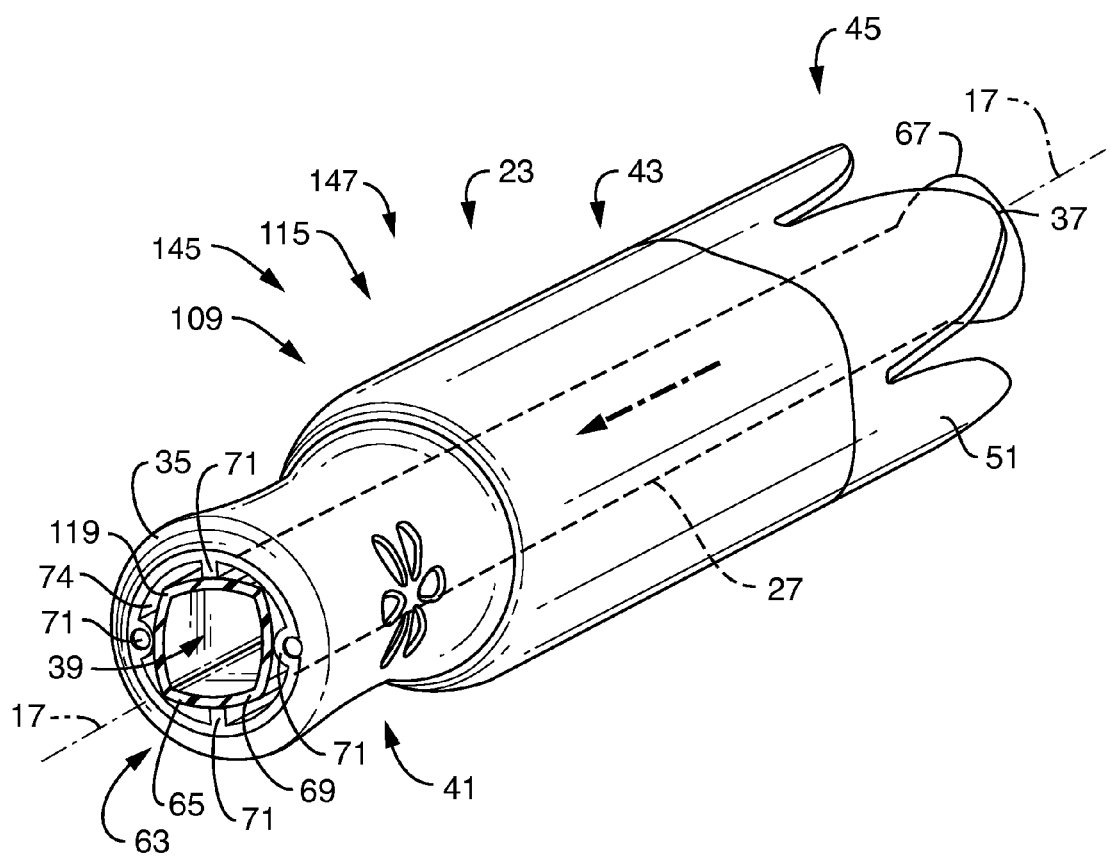
FIG. 13 is a second perspective view of the step illustrated in FIG. 12.
Figure 14:
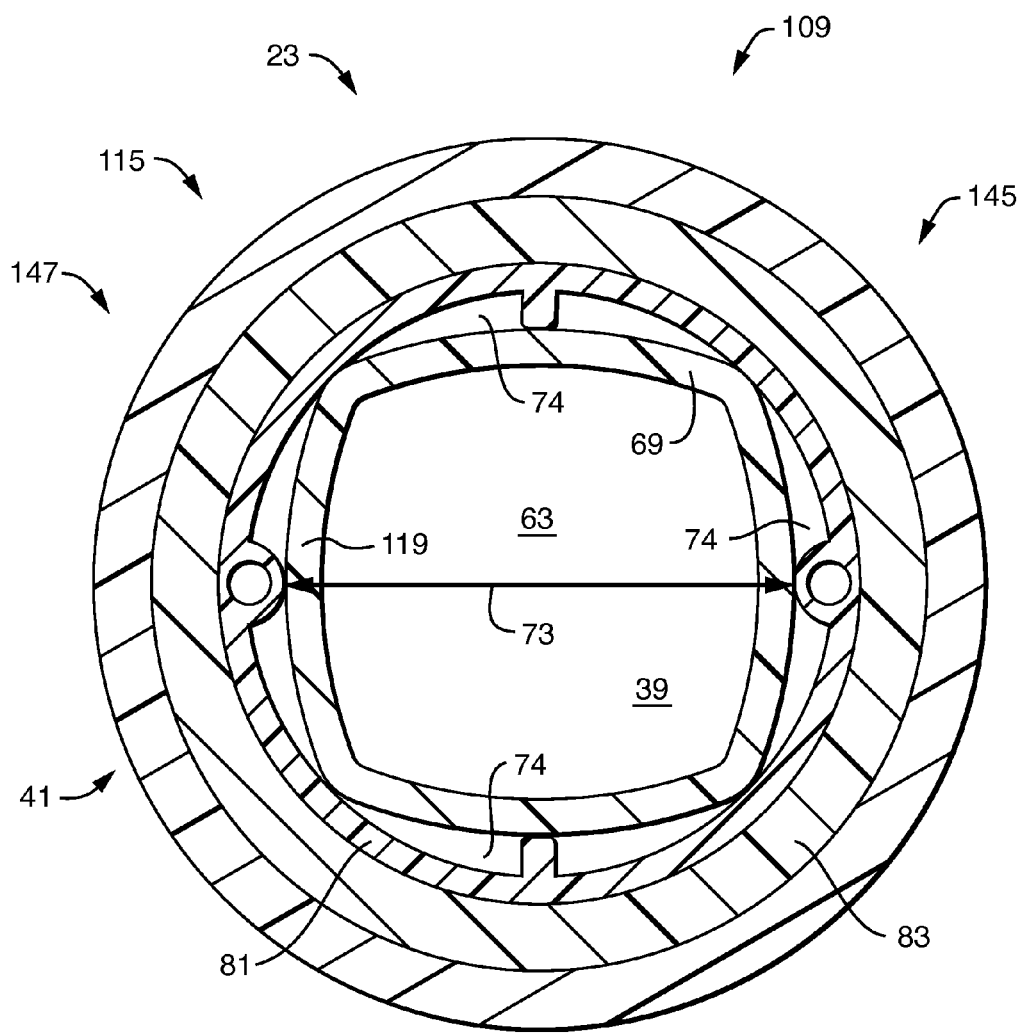
FIG. 14 is an end view of the partially assembled tampon applicator of FIG. 13.
Figure 15:
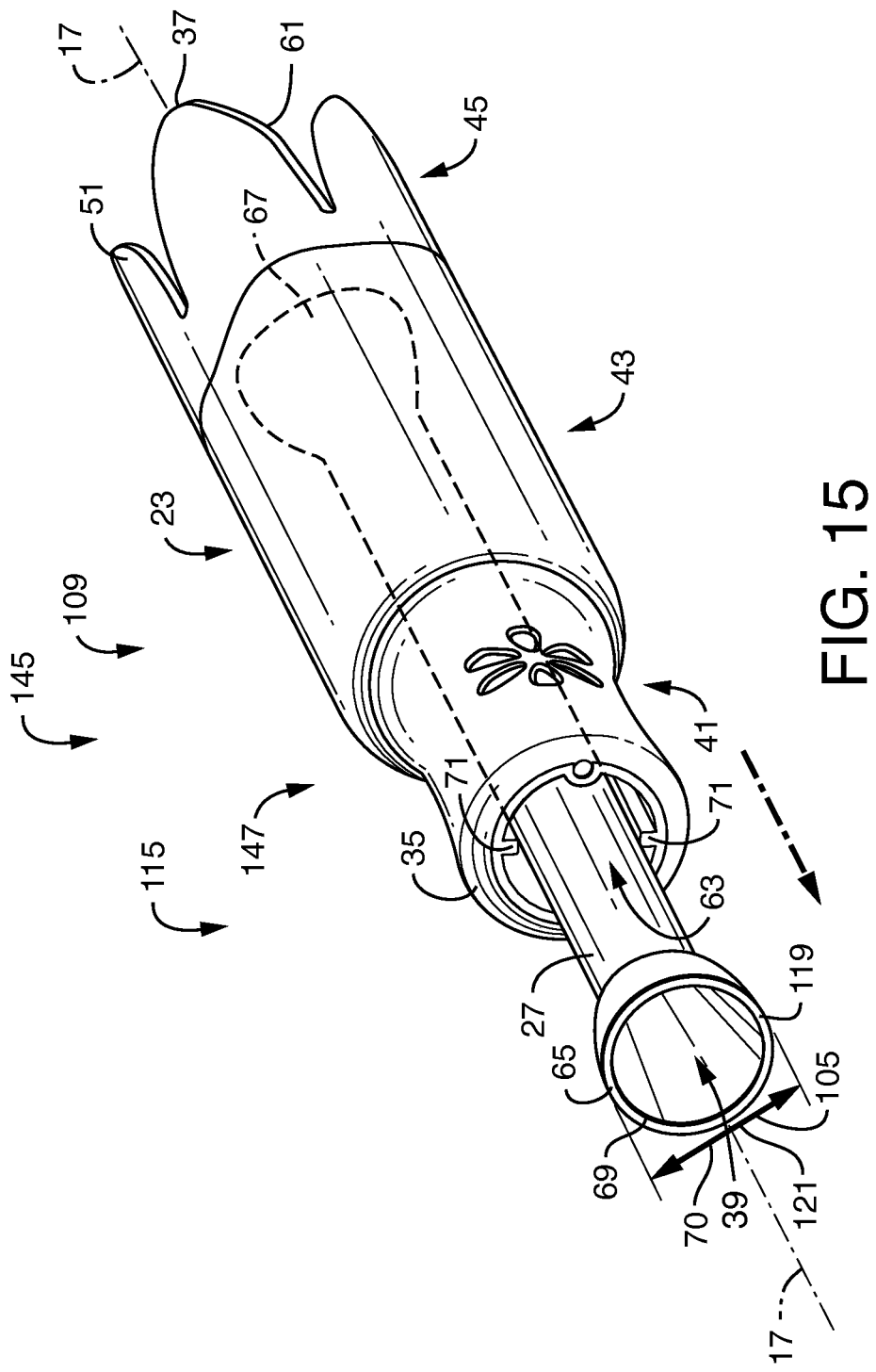
FIG. 15 is a perspective view of another step in the first method for assembling the tampon applicator of FIG. 1.

The present invention also provides a method of assembling a tampon applicator like those described herein. Referring now to FIGS. 11-15, a first exemplary method 109 is illustrated. Specifically, FIG. 11 representatively illustrates a perspective view of the first steps in the first method 109 for assembling tampon applicators like those illustrated in FIG. 1. FIG. 12 representatively illustrates a perspective view of another step in the method 109. FIG. 13 representatively illustrates a second perspective view of the step illustrated in FIG. 12. FIG. 14 is an end view of the partially assembled tampon applicator of FIG. 13. FIG. 15 representatively illustrated a perspective view of another step in the first method 109 for assembling tampon applicators like those illustrated in FIG. 1.

Generally, the first method includes the step of providing a barrel like those described herein. In a specific embodiment, the first method 109 includes the step 111 of providing a barrel 23 having an insertion end 37, a plunger end 35, and a plurality of internal ridges 71 (FIG. 11). The internal ridges 71 define a guide channel 63 having an effective diameter 73 (FIG. 14). The internal ridges 71 have a leading end 93 and a trailing end 95 (FIG. 5).

The first method further includes the step of providing a plunger like those described herein. In specific embodiments, the first method 109 further includes the step 113 of providing a plunger 27 having a finger-contacting end 65, a tampon-contacting end 67, and a flare 119 on at least one of the finger-contacting end 65 or the tampon-contacting end 67. The flare 119 has an effective flare diameter 121 that is greater than the effective diameter 73 of the guide channel 63.

Referring now to FIG. 12, the method 109 further includes the step 115 of assembling the plunger 27 and the barrel 23. The assembling step 115 includes pushing the flare 119 into the guide channel 63 and deforming the flare 119 while moving the flare 119 through the guide channel 63. Finally, the method 109 includes the step of reestablishing the flare 119 after the flare 119 exits the guide channel 63.

In specific embodiments of the method 109, the plunger 27 includes a finger flare 69 on the finger-contacting end 65 having an effective finger flare diameter 105 (FIG. 11) that is greater than the effective diameter of the guide channel 63 (FIG. 14). In these embodiments, and as illustrated in FIG. 12, the assembling step 115 further includes first moving the finger-contacting end 65 of the plunger 27 through the insertion end of the barrel 37. Second, the assembling step 115 includes contacting the leading end 93 of the internal ridges 71 with the finger flare 69 of the plunger 27. Third, the assembling step 115 includes pushing the finger flare 69 into the guide channel 63. Fourth, the assembling step 115 includes deforming the finger flare 69 while moving the finger flare 69 through the guide channel 63. For example, FIGS. 13 and 14 representatively illustrate the finger flare 69 in the deformed condition as the finger flare 69 moves through the guide channel 63 defined by the ridges 71. Fifth, the assembling step 115 includes reestablishing the shape of the finger flare 69 after the finger flare 69 exits the guide channel 63 as illustrated in FIG. 15.

Figure 16:
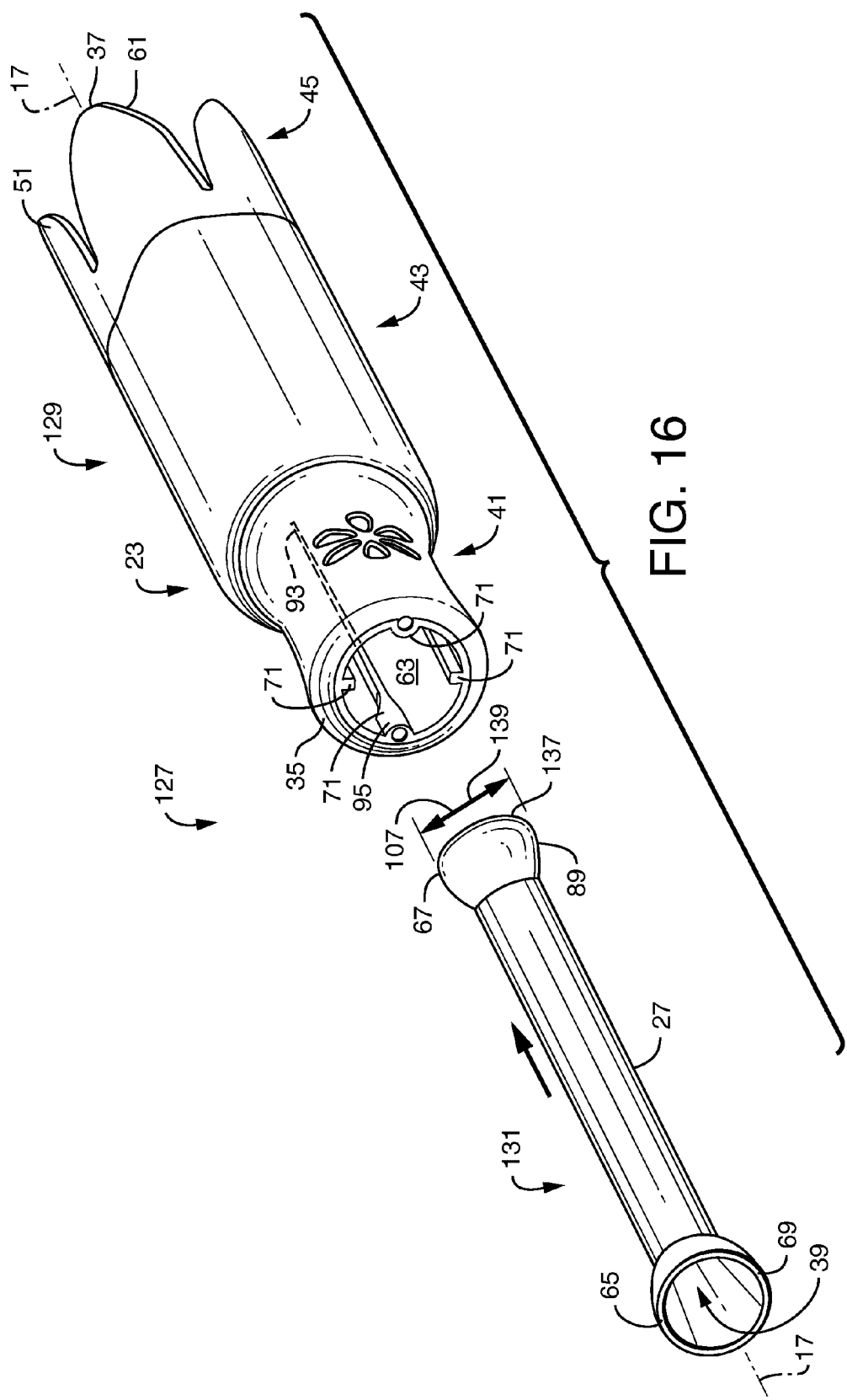
FIG. 16 is a perspective view of the first steps in a second method for assembling the tampon applicator of FIG. 1.
Figure 17:
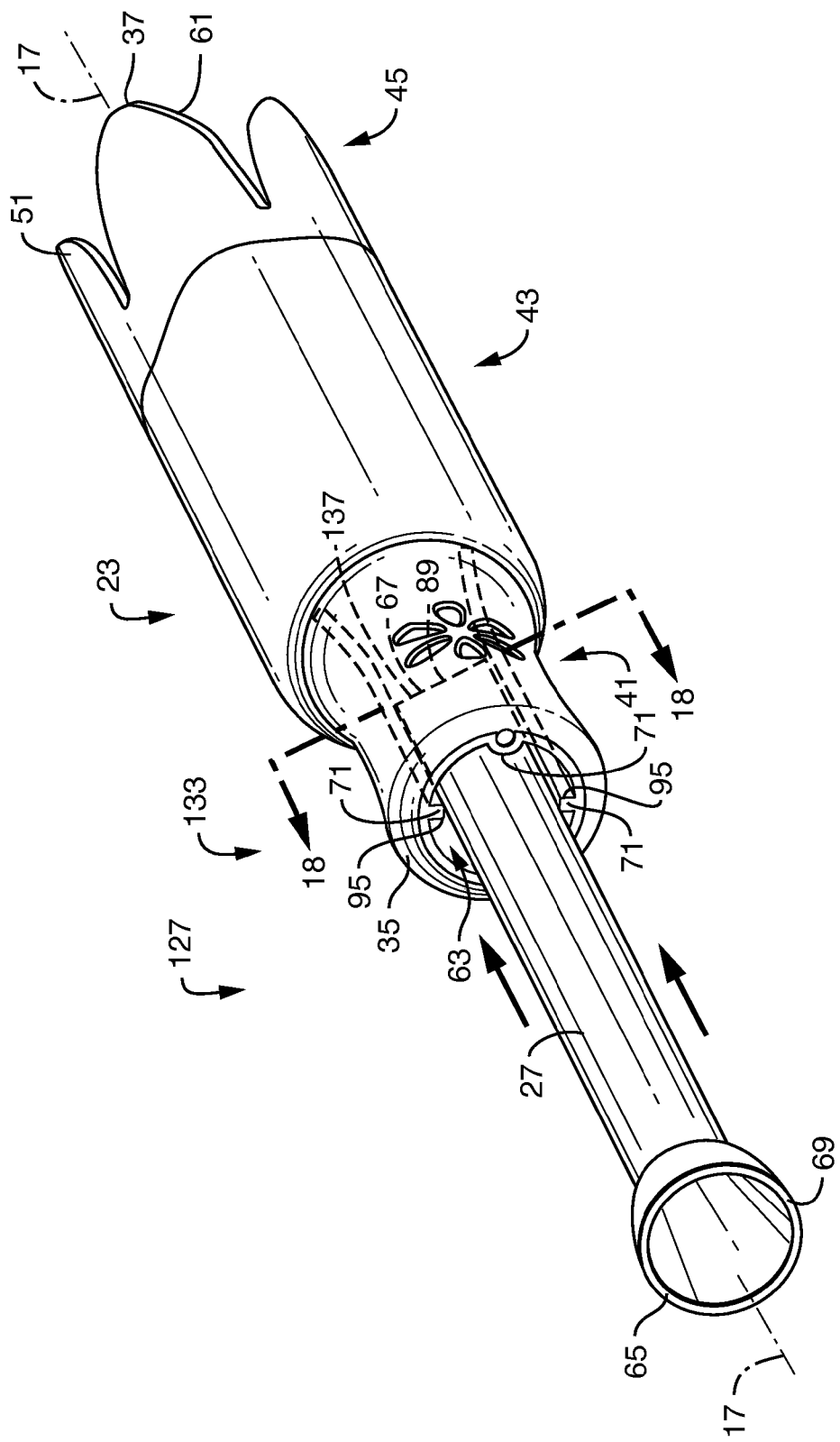
FIG. 17 is a perspective view of another step in the second method for assembling the tampon applicator of FIG. 1.
Figure 18:
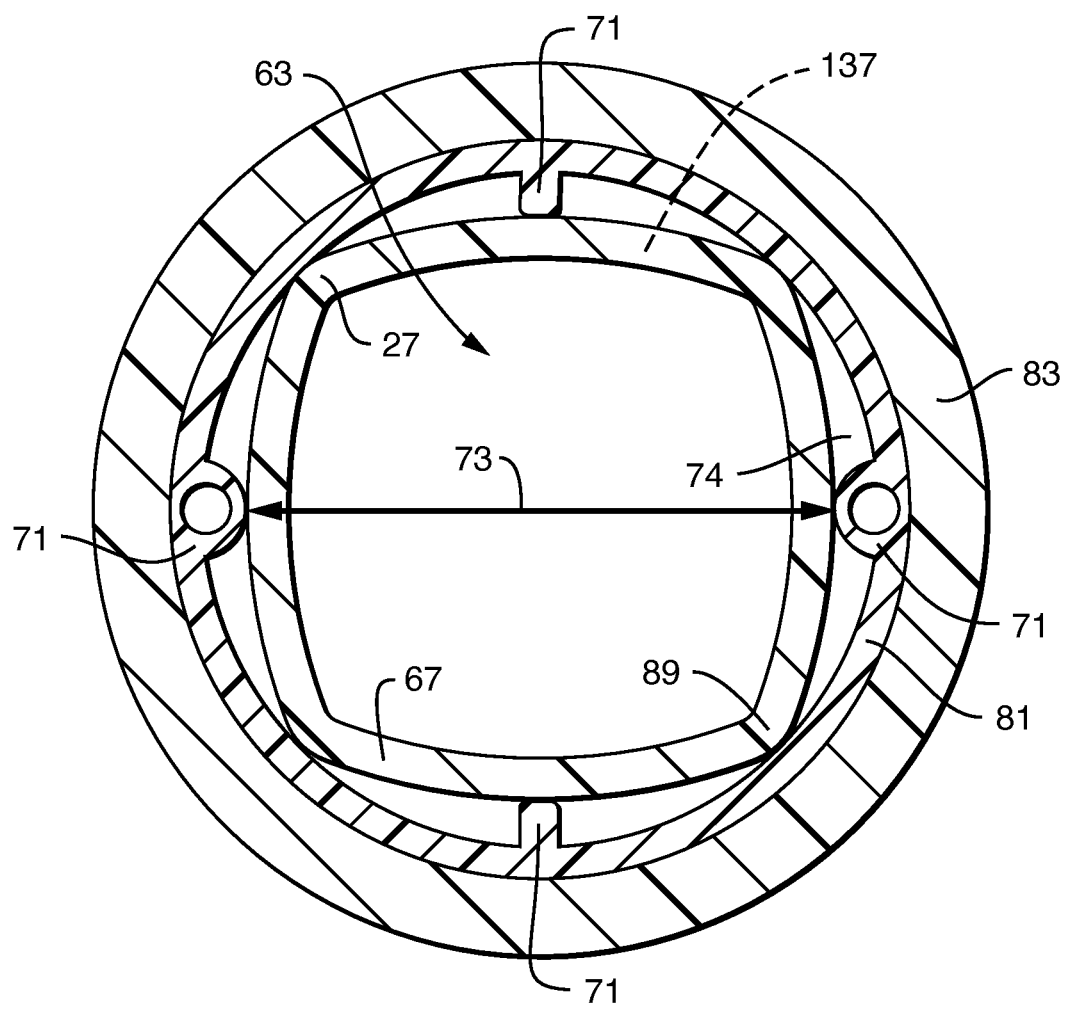
FIG. 18 is a cross sectional view of the partially assembled tampon applicator of FIG. 17 taken along the line 18-18.
Figure 19:
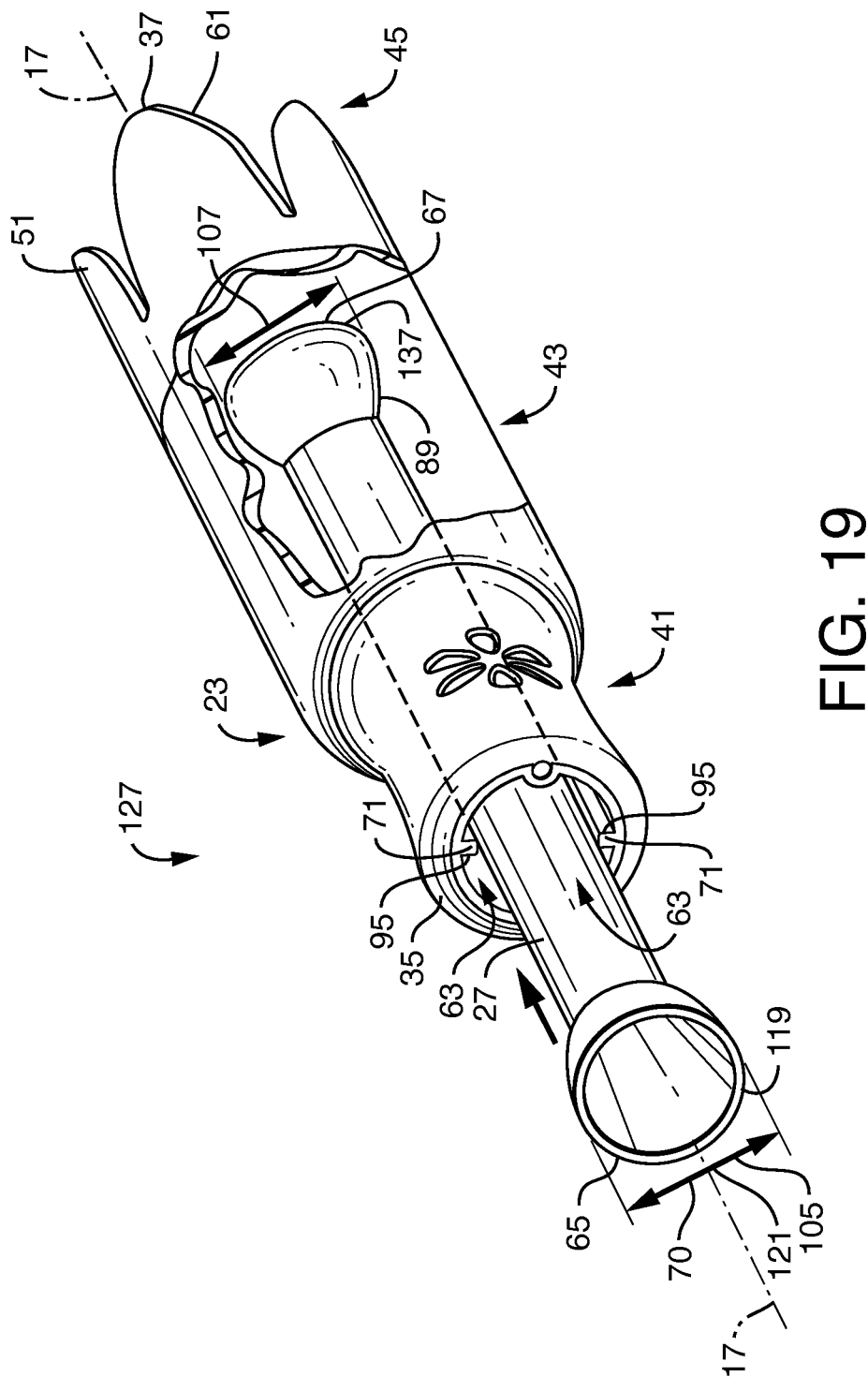
FIG. 19 is a perspective view of another step in the second method for assembling the tampon applicator of FIG. 1 with portions cut away to illustrate internal elements.

Referring now to FIGS. 16-19, a second exemplary method 127 is illustrated. Specifically, FIG. 16 representatively illustrates a perspective view of the first steps in a second method 127 for assembling tampon applicators like those described herein. FIG. 17 is a perspective view of another step in the second method 127. FIG. 18 is a cross sectional view of the partially assembled tampon applicator of FIG. 17 taken along the line 18-18. FIG. 19 is a perspective view of another step in the second method 127 for assembling tampon applicators with portions of the barrel cut away to better illustrate internal elements.

Generally, the second method includes the step of providing a barrel like those described herein. In a specific embodiment, the second method 127 includes the step 129 of providing a barrel 23 having an insertion end 37, a plunger end 35, and a plurality of internal ridges 71 (FIG. 16). The internal ridges 71 define a guide channel 63 having an effective diameter 73 (FIG. 18). The internal ridges 71 have a leading end 93 and a trailing end 95 as illustrated in FIGS. 5 and 16.

The method further includes the step of providing a plunger like those described herein. In specific embodiments, the second method 127 further includes the step 131 of providing a plunger 27 having a finger-contacting end 65, a tampon-contacting end 67, and a flare 137 on at least one of the finger-contacting end 65 or the tampon-contacting end 67. The flare 137 has an effective flare diameter 139 that is greater than the effective diameter 73 (FIG. 18) of the guide channel 63.

Referring now to FIG. 17, the second method 127 further includes the step 133 of assembling the plunger 27 and the barrel 23. The assembling step 133 includes pushing the flare 137 into the guide channel 63 and deforming the flare 137 while moving the flare 137 through the guide channel 63. Finally, the method 127 includes the step of reestablishing the flare 137 after the flare 137 exits the guide channel 63 as illustrated in FIG. 19.

In specific embodiments of the second method 127, the plunger 27 includes a tampon flare 89 on the tampon-contacting end 67 having an effective tampon flare diameter 107 that is greater than the effective diameter 73 of the guide channel 63 (FIG. 18). In these embodiments, and as illustrated in FIG. 17, the assembling step 133 further includes first moving the tampon-contacting end 67 of the plunger 27 through the plunger end 35 of the barrel 23. Second, the assembling step 133 includes contacting the trailing end 95 of the internal ridges 71 with the tampon flare 89 of the plunger 27. Third, the assembling step 133 includes pushing the tampon flare 89 into the guide channel 63. Fourth, the assembling step 133 includes deforming the tampon flare 89 while moving the tampon flare 89 through the guide channel 63 as illustrated in FIGS. 17 and 18. Fifth, the assembling step 133 includes reestablishing the shape of the tampon flare 89 after the tampon flare 89 exits the guide channel 63 as illustrated in FIG. 19.

In another aspect of the present invention, a method of assembling a tampon applicator, e.g., like those disclosed herein, includes the steps of providing a barrel, providing a plunger, assembling the plunger and barrel, inserting a tampon, and bending petals closed to substantially enclose the tampon within the barrel. Referring again to FIG. 11, the first steps in a third method 145 for assembling a tampon applicator like that of FIG. 1 are illustrated. The third method 145 includes the step 111 of providing a barrel 23. The barrel 23 has an insertion end 37 with petals 51, a plunger end 35, and a plurality of internal ridges 71. The internal ridges 71 define a guide channel 63 having an effective diameter 73 (FIG. 14). The internal ridges 71 have a leading end 93 and a trailing end 95.

The third method 145 further includes the step 113 of providing a plunger 27 as illustrated in FIG. 11. The plunger 27 has a finger-contacting end 65, a tampon-contacting end 67, a finger flare 69 on the finger-contacting end 65, a tampon flare 89 on the tampon-contacting end 67. The finger flare 69 has a circular shape and has a flare diameter 70 that is at least 15% larger than the effective diameter 73 (FIG. 14) of the guide channel 63.

The third method 145 further includes the step 115 of assembling the plunger 27 and the barrel 23 as illustrated in FIG. 12. The step 115 of assembling includes first moving the finger-contacting end 65 of the plunger 27 through the insertion end 37 of the barrel 23. Second, the step 115 of assembling includes contacting the leading end 93 of the internal ridges 71 with the finger flare 69 of the plunger 27. Third, the step 115 of assembling includes deforming the finger flare 69 of the plunger 27 into a non-circular shape while moving the finger flare 69 from the leading end 93 of the internal ridges 71 to the trailing end 95 of the internal ridges 71 as illustrated in FIGS. 13 and 14. Fourth, the step 115 of assembling includes moving the finger-contacting end 65 of the plunger 27 out of the plunger end 35 of the barrel 23. Fifth, the step 115 of assembling includes reestablishing the circular shape of the finger flare 69 as illustrated in FIG. 15.

Figure 20:
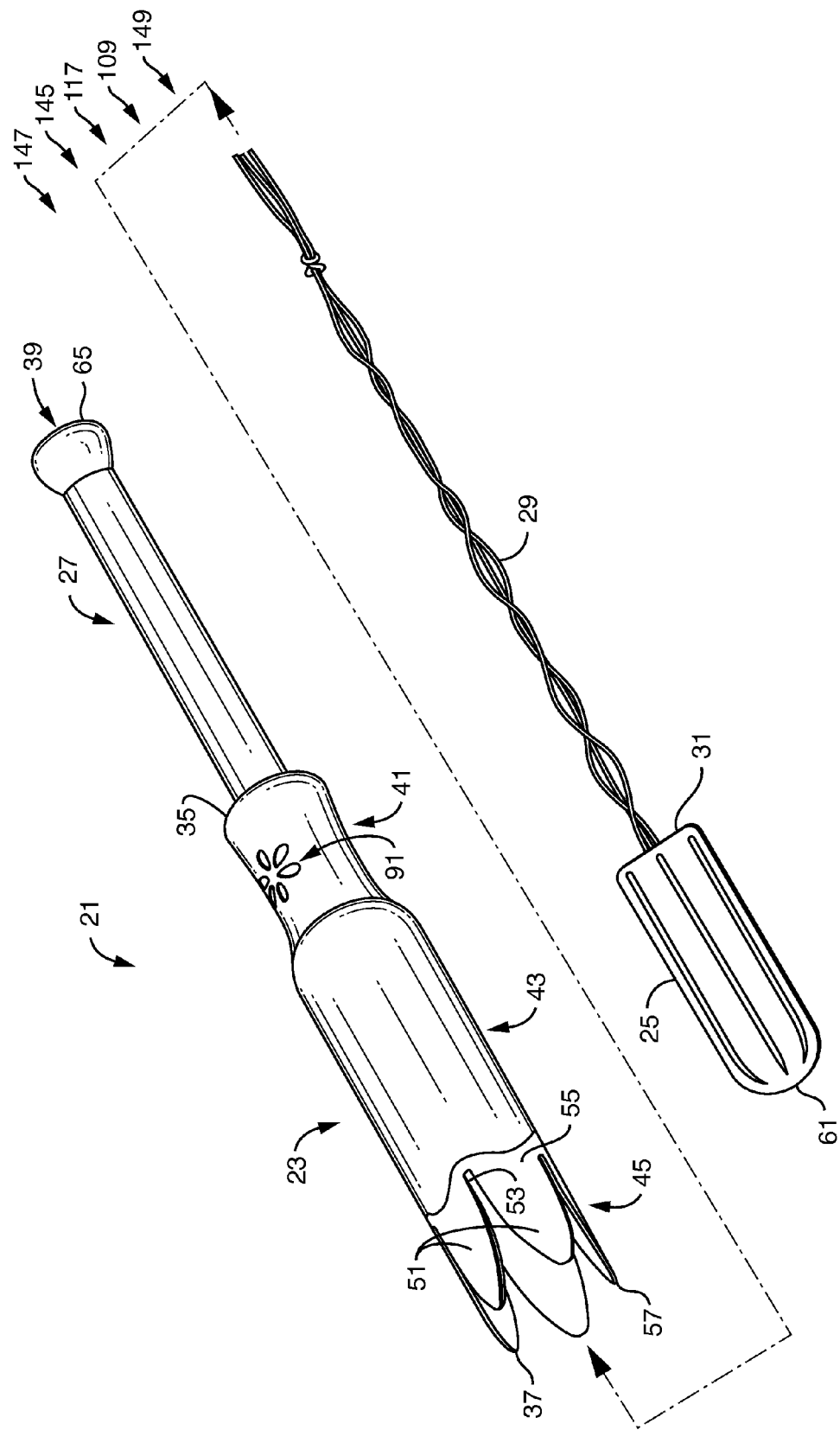
FIG. 20 is a perspective view of another step in either the first or the second method for assembling a tampon applicator.
Figure 21:
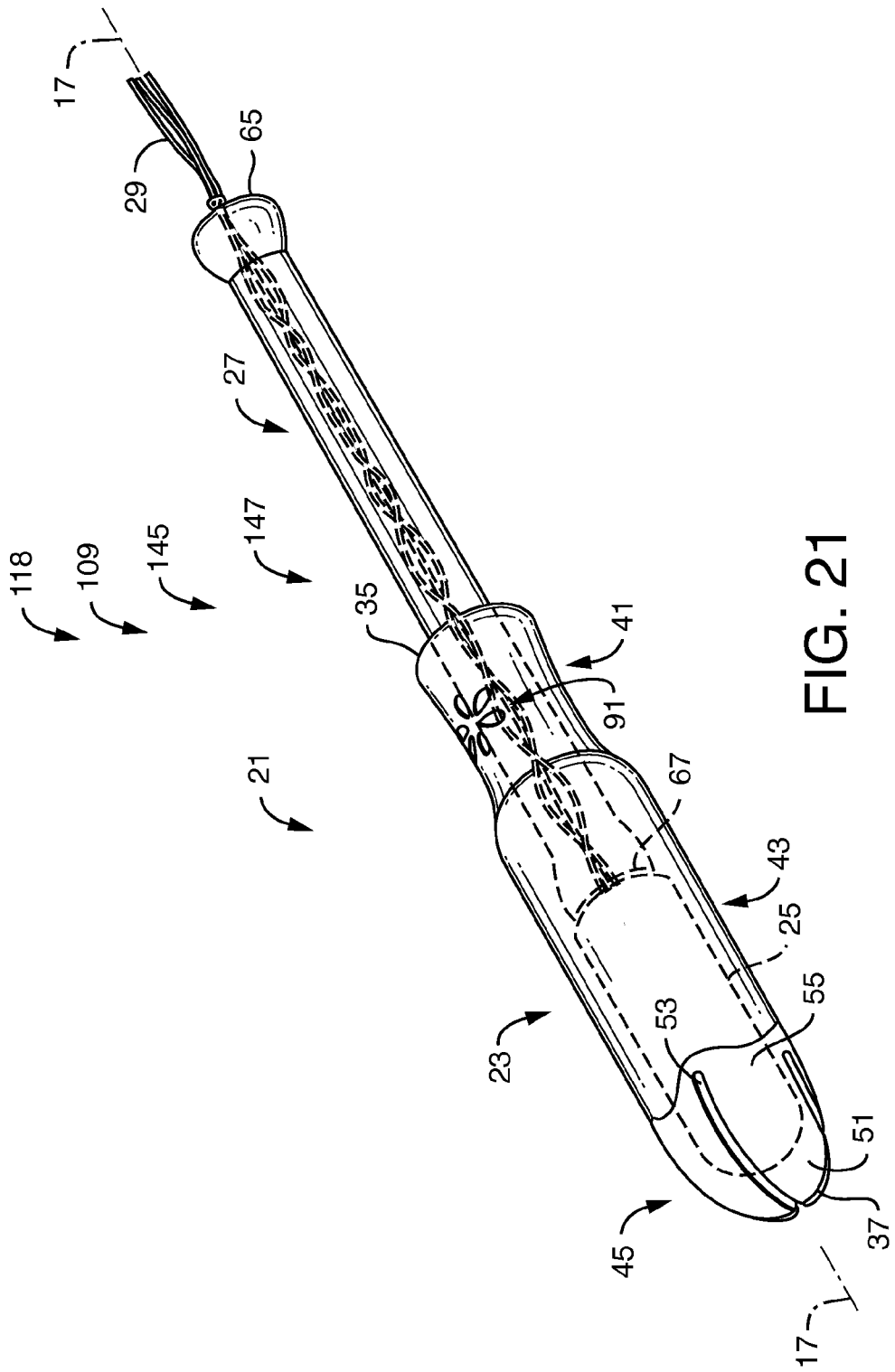
FIG. 21 is a perspective view of another step in either the first or the second method for assembling a tampon applicator.

The third method 145 further includes the step 117 of inserting a tampon 25 having a withdrawal string 29 into the insertion end 37 of the barrel 23 after assembling the plunger 27 and the barrel 23 as illustrated in FIG. 20. Finally, the third method 145 includes the step 118 of bending the petals 51 closed to substantially enclose the tampon 25 within the barrel 23 as illustrated in FIG. 21. The step of bending the petals 51 closed may be completed before or after the plunger 27 and the barrel 23 are assembled. Likewise, the step of bending the petals 51 closed may be completed before or after the tampon 25 is inserted. Finally, the step of bending the petals 51 may be completed during the formation of the barrel 23 (not illustrated) or may be completed in a post production step as illustrated in FIGS. 21 and 22.

In another aspect of the present invention, a method of assembling a tampon applicator, e.g., like those disclosed herein, includes the steps of providing a barrel, providing a plunger, assembling the plunger and the barrel, inserting a tampon, passing a withdrawal string through the plunger, and bending the petals closed to substantially enclose the tampon within the barrel. Referring again to FIG. 11, the first steps in a fourth method 147 for assembling a tampon applicator like those described herein are illustrated. The fourth method 147 includes the step 111 of providing a barrel 23 made of low density polyethylene. The barrel 23 has an insertion end 37 with petals 51, a plunger end 35, a grip region 41, a central region 43, and a tip region 45, and a plurality of internal ridges 71. The internal ridges 71 define a guide channel 63 having an effective diameter 73 (FIG. 14). The internal ridges 71 have a leading end 93 and a trailing end 95. The grip region 41 has a reduced diameter 72 as compared to the diameter 28 of the central region 43. The ridges 71 are located primarily in the grip region 41.

The fourth method 147 further includes the step 113 of providing a plunger 27 made of low density polyethylene. The plunger 27 has a finger-contacting end 65, a tampon-contacting end 67, a finger flare 69 on the finger-contacting end 65, a tampon flare 89 on the tampon-contacting end 67. The plunger 27 also includes a hollow channel 39 extending from the finger-contacting end 65 to the tampon-contacting end 67. The finger flare 69 has a circular shape and has a finger flare diameter 70 that is at least 15% larger than the effective diameter 73 (FIGS. 11 and 14) of the guide channel 63.

The fourth method 147 further includes the step 115 of assembling the plunger 27 and the barrel 23. The assembly step 115 includes first moving the finger-contacting end 65 of the plunger 27 through the insertion end 37 of the barrel 23. Second, the assembly step 115 includes contacting the leading end 93 of the internal ridges 71 with the finger flare 69 of the plunger 27. Third, the assembly step 115 includes deforming the finger flare 69 of the plunger 27 into a non-circular shape while moving the finger flare 69 from the leading end 93 of the internal ridges 71 to the trailing end 95 of the internal ridges 71 as illustrated in FIG. 13. Fourth, the assembly step 115 includes moving the finger-contacting end 65 of the plunger 23 out of the plunger end 35 of the barrel 23. Fifth, the assembly step 115 includes reestablishing the circular shape of the finger flare 69 as illustrated in FIG. 15.

The fourth method 147 further includes the step 117 of inserting a tampon 25 having a withdrawal string 29 into the insertion end 37 of the barrel 23 after assembling the plunger 27 and the barrel 23 as illustrated in FIG. 20.

The fourth method 147 further includes the step 149 of passing the withdrawal string 29 through the hollow channel 39 of the plunger 27 (FIGS. 20 and 21). Finally, the method 147 further includes the step 118 of bending the petals 51 closed to substantially enclose the tampon 25 within the barrel 23 as illustrated in FIG. 21.

Any of the barrels, tampons, plungers, ridges, and the like described herein may be used in any combination with any of the methods, or steps within the methods, described herein. For example, in any of the methods described herein, the barrel 23 may define a circumference at the plunger end 35 and may have four internal ridges 71 evenly spaced about the circumference.

In another example, any of the methods described herein may include the step of providing a plunger 27 having a hollow channel 39 extending from the finger-contacting end 65 to the tampon-contacting end 67 as described and illustrated herein. In these embodiments, any of the methods may further include the step of inserting a tampon 25 having a withdrawal string 29 into the insertion end 37 of the barrel 23 after the assembling step and passing the withdrawal string 29 through the hollow channel 39 of the plunger 27.

In another example, any of the methods described herein may include the step of providing a plunger 27 having a finger flare 69 that has a circular shape. In these embodiments, the finger flare 69 may have the circular shape before and after the assembling step and may have a non-circular shape while moving the finger flare 69 through the guide channel 63.

In another example, any of the methods described herein may also include the step of providing a barrel 23 wherein the insertion end 37 includes petals 51, e.g., like those described herein. In these embodiments, any of the methods may further include the step of bending the petals 51 closed to substantially enclose the tampon 25 within the barrel 23 before or after the assembling step.

In another example, any of the methods described herein may also include the step of providing a barrel 23 wherein the effective diameter of the guide channel 63 as measured at the leading end 93 of the ridges 71 is greater than the effective diameter 73 of the guide channel 63 as measured at the trailing end 95 of the ridges 71 as described herein.

While the invention has been described in detail with respect to specific embodiments thereof, it will be appreciated that those skilled in the art, upon attaining understanding of the foregoing, will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. A method of assembling a tampon applicator comprising,
    providing a barrel, wherein the barrel has an insertion end, a plunger end, a grip region adjacent the plunger end, a central region longitudinally adjacent the grip region, and a plurality of internal ridges located in the grip region, wherein the plurality of internal ridges define a guide channel having an effective diameter, and wherein the plurality of internal ridges have a leading end and a trailing end;
    providing a plunger, wherein the plunger has a finger-contacting end, a tampon contacting end, and a flare on at least one of the finger-contacting end or the tampon-contacting end and wherein the flare has an effective flare diameter that is greater than the effective diameter of the guide channel; and
    assembling the plunger and the barrel by
    pushing the flare into the guide channel,
    deforming the flare while moving the flare through the guide channel, and
    reestablishing the flare after the flare exits the guide channel.

2. The method of claim 1 wherein the plunger includes a finger flare on the finger-contacting end having an effective finger flare diameter that is greater than the effective diameter of the guide channel and wherein the assembling step further includes the steps of
    first, moving the finger-contacting end of the plunger through the insertion end of the barrel,
    second, contacting the leading end of the plurality of internal ridges with the finger flare of the plunger,
    third, pushing the finger flare into the guide channel,
    fourth, deforming the finger flare while moving the finger flare through the guide channel, and
    fifth, reestablishing the finger flare after the finger flare exits the guide channel.

3. The method of claim 2 wherein the finger flare has a circular shape before and after the assembling step and has a non-circular shape while moving through the guide channel.

4. The method of claim 3 Wherein the insertion end of the barrel includes petals and the method further includes the step of bending the petals closed to substantially enclose the tampon within the barrel.

5. The method of claim 1 wherein the plunger includes a tampon flare on the tampon-contacting end having an effective tampon flare diameter that is greater than the effective diameter of the guide channel and wherein the assembling step further includes the steps of
    first, moving the tampon-contacting end of the plunger through the plunger end of the barrel, second, contacting the trailing end of the plurality of internal ridges with the tampon flare of the plunger, third, pushing the tampon flare into the guide channel, fourth, deforming the tampon flare while moving the tampon flare through the guide channel, and fifth, reestablishing the tampon flare after the tampon flare exits the guide channel.

6. The method of claim 1 wherein the effective flare diameter is at least 15% larger than the effective diameter of the guide channel.

7. The method of claim 1 wherein the barrel has three internal ridges.

8. The method of claim 1 wherein the barrel defines a circumference at the plunger end and has four internal ridges evenly spaced about the circumference.

9. The method of claim 1 wherein the plunger includes a hollow channel extending from the finger-contacting end to the tampon-contacting end.

10. The method of claim 9 farther including the step of inserting a tampon having a withdrawal string into the insertion end of the barrel after the assembly step and passing the withdrawal string through the hollow channel of the plunger.

11. The method of claim 1 wherein the effective diameter of the guide channel as measured at the leading end of the ridges is greater than the effective diameter of the guide channel as measured at the trailing end of the ridges.

12. The method of claim 1 wherein the barrel is constructed of a polymeric core layer and the grip region is constructed of a thermoplastic elastomer applied over the polymeric core layer of the barrel.

13. The method of claim 1 wherein the central region of the barrel is constructed of a core layer having an outer surface and the grip region is constructed of a skin layer applied over the core layer of the barrel and each of the outer surface of the central region of the barrel and the skin layer of the grip region has a coefficient of friction and further wherein the coefficient of friction of the grip region is higher than the coefficient of friction of the outer surface of the central region of the barrel.

14. A method of assembling a tampon applicator comprising, providing a barrel, wherein the barrel has an insertion end with petals, a plunger end, a grip region adjacent the plunger end, a central region longitudinally adjacent the grip region, and a plurality of internal ridges located in the grip region, wherein the plurality of internal ridges define a guide channel having an effective diameter, and wherein the plurality of internal ridges have a leading end and a trailing end;

providing a plunger, wherein the plunger has a finger-contacting end, a tampon-contacting end, a finger flare on the finger-contacting end, a tampon flare on the tampon-contacting end, and wherein the finger flare has a circular shape and has a flare diameter that is at least 15% larger than the effective diameter of the guide channel;

assembling the plunger and the barrel by first, moving the finger-contacting end of the plunger through the insertion end of the barrel, second, contacting the leading end of the plurality of internal ridges with the finger flare of the plunger, third, pushing the finger flare into the guide channel, fourth, deforming the finger flare into a non-circular shape while moving the finger flare through the guide channel from the leading end of the internal ridges to the trailing end of the internal ridges, and fifth, moving the finger flare out of the plunger end of the barrel, and sixth, reestablishing the circular shape of the finger flare;

inserting a tampon having a withdrawal string into the insertion end of the barrel after assembling the plunger and the barrel; and bending the petals closed to substantially enclose the tampon within the barrel.

15. The method of claim 14 wherein the plunger includes a hollow channel extending from the finger-contacting end to the tampon-contacting end and the method further includes the step of passing the withdrawal string through the hollow channel of the plunger.

16. The method of claim 15 wherein the tampon flare has a flare diameter greater than the flare diameter of the finger flare.

17. The method of claim 15 wherein the grip region has a reduced diameter as compared to the central region and wherein the ridges are located primarily in the grip region.

18. The method of claim 17 wherein the barrel has four internal ridges and each ridge has a ridge height of about 0.8 mm at the trailing end.

19. The method of claim 17 wherein the effective diameter of the guide channel as measured at the leading end of the ridges is greater than the effective diameter of the guide channel as measured at the trailing end of the ridges.

20. The method of claim 14 wherein the barrel is constructed of a polymeric core layer and the grip region is constructed of a thermoplastic elastomer applied over the polymeric core layer of the barrel.

21. The method of claim 14 wherein the central region of the barrel is constructed of a core layer having an outer surface and the grip region is constructed of a skin layer applied over the core layer of the barrel and each of the outer surface of the central region of the barrel and the skin layer of the grip region has a coefficient of friction and further wherein the coefficient of friction of the grip region is higher than the coefficient of friction of the outer surface of the central region of the barrel.

* * * * *